United States Patent [19]

Teter et al.

[11] Patent Number: 6,106,562

[45] Date of Patent: Aug. 22, 2000

[54] APPARATUS AND METHODS FOR PREDICTING PHYSICAL AND CHEMICAL PROPERTIES OF MATERIALS

[75] Inventors: Michael P. Teter, Corning, N.Y.; Michael C. Payne, Cambridge, United Kingdom

[73] Assignee: Corning Incorporated, Corning, N.Y.

[21] Appl. No.: 07/935,545

[22] Filed: Aug. 26, 1992

Related U.S. Application Data

[63] Continuation of application No. 07/490,750, Mar. 8, 1990, abandoned.

[51] Int. Cl.⁷ .................................................. G06F 17/50
[52] U.S. Cl. ................................. 703/12; 703/2; 700/268
[58] Field of Search ...................... 364/499, 578, 364/806, 497, 498, 572, 527, 724.04, 924.4; 526/75; 564/69; 585/401, 501; 935/88; 700/268; 703/2, 12

[56] References Cited

U.S. PATENT DOCUMENTS

| | | |
|---|---|---|
| 4,719,582 | 1/1988 | Ishida et al. . |
| 4,797,842 | 1/1989 | Nackman et al. . |
| 4,809,202 | 2/1989 | Wolfram . |
| 4,819,161 | 4/1989 | Konno et al. . |
| 4,908,781 | 3/1990 | Levinthal et al. . |
| 5,260,882 | 11/1993 | Bianco et al. .......................... 364/496 |
| 5,331,573 | 7/1994 | Balaji et al. ............................ 364/497 |
| 5,420,805 | 5/1995 | Still et al. ............................... 364/496 |
| 5,434,796 | 7/1995 | Weininger ............................... 364/496 |
| 5,463,564 | 10/1995 | Agrafiotis et al. ..................... 364/496 |
| 5,499,193 | 3/1996 | Sugawara et al. ...................... 364/496 |

OTHER PUBLICATIONS

Allan et al., "Nonlocal Pseudopotentials in Molecular–Dynamical Density–Functional Theory," *Phys. Rev. Lett.*, 59, 1136–1139 (1987).

Borman, S., "Improved Access to Supercomputers Boosts Chemical Applications," *Chemical & Engineering News*, Jul. 17, 1989, pp. 29–32, 35–37.

Car, et al., "Unified Approach for Molecular Dynamics and Density–Functional Theory," *Phys. Rev. Lett.*, 55, 2471–2474 (1985).

Davidson, E. R., "The Iterative Calculation of a Few of the Lowest Eigenvalues and Corresponding Eigenvectors of Large Real–Symmetric Matrices", *J. Comput. Phys.*, 17, 87–94, (1975).

Haydock, R., "The Recursive Solution of the Schrodinger Equation," *Solid State Physics*, 35, 215–294 (1980).

Hestenes, et al., "Methods of Conjugate Gradients for Solving Linear System," *J. Res. Nat. Bur. Stand.*, 49, 409–436, (1952).

Payne, et al., "Molecular Dynamics and ab Initio Total Energy Calculations," *Phys. Rev. Lett.*, 56, 2656, (1986).

Stich, et al., "Conjugate Gradient Minimization of the Energy Functional," *Phys. Rev. B.*, 39, 4997–5004, (1989).

Vanderbilt, et al., "Total energies of diamond (111) surface reconstructions by a linear combination of atomic orbitals method," *Phys. Rev. B.*, 30, 6118–6130 (1984).

Wood, et al., "A New Method for Diagonalising Large Matrices," *J. Phys. A: Math. Gen.*, 18, 1343–1359 (1985).

*Primary Examiner*—Dung C. Dinh
*Attorney, Agent, or Firm*—Alfred L. Michaelsen; Maurice M. Klee

[57] ABSTRACT

Improved methods and apparatus for predicting physical properties of complex materials are provided. The physical properties are predicted from the electronic structure of the material. The electronic structure is determined using an iterative, computer-based technique. The iterative technique has been found to have a rate of convergence at least an order of magnitude faster than prior techniques for determining electronic structures. Among other applications, the invention is used to prepare materials having selected physical properties under selected conditions.

20 Claims, 7 Drawing Sheets

PRIMARY FLOW CHART

BAND CORRECTION FLOW CHART

APPARATUS AND METHODS FOR PREDICTING PHYSICAL AND CHEMICAL PROPERTIES OF MATERIALS

This application is a continuation application of application Ser. No. 07/490,750, filed on Mar. 8, 1990 (abandoned).

FIELD OF THE INVENTION

This invention relates to apparatus and methods for predicting physical and chemical properties of materials. More particularly, the invention relates to apparatus and methods for determining the quantum mechanical electronic structure of a material and using that structure to predict the material's properties. The invention also relates to the preparation of materials having selected physical or chemical properties based on the prediction of those properties from the material's electronic structure.

DESCRIPTION OF THE TECHNOLOGY

I. Introduction

Quantum mechanical electronic structures have been determined for a variety of atoms, molecules and materials. From such electronic structures, predictions have been made of a variety of physical and chemical properties, including lattice spacings, bond angles, surface energies, absorption spectra, refractive indices, optical activities, magnetic susceptibilities, magnetic resonance characteristics, piezoelectric properties, bond energies, catalytic activities, molecular structures, physical property changes under high pressure, and the like.

Similarly, materials having selected physical or chemical properties under selected conditions have been prepared based on the prediction of such properties from electronic structures. For example, using the quantum mechanical electronic structure for carbon, O. H. Nielsen of Denmark predicted the complete nonlinear elastic behavior for diamond. He predicted the crystal axis which should most strongly resist collapse under high pressure. He also predicted the transition of diamond from an insulator to a semimetal at large uniaxial compressive stresses (pressures about 4 Mbar). Workers using diamond anvils for high pressure studies have since found all of these predictions to be verified. See O. H. Nielsen, *Phys. Rev. B*, 34, 5808 (1986). More generally, electronic structures have been used to design numerous new materials ranging from semiconductors to pharmaceutical preparations.

The present invention relates to improved methods and apparatus for determining electronic structures of materials and to the use of those structures 1) to predict physical and chemical properties of materials and 2) to prepare materials having desired properties. Before turning to the details of the invention, a general discussion of the field of electronic structure determinations will be presented. Further discussions of this field can be found in various textbooks and reference works, including "Density Functional Methods: Theory and Applications," J. Callaway and N. H. March, *Solid State Physics*, 38, 135 (1984), which summarizes the use of density functional theory in quantum mechanics through 1983. The relevant portions of this reference, as well as those of the references cited therein, are incorporated herein by reference.

A general discussion of the application of supercomputers to problems in chemical synthesis, including the determinations of quantum mechanical structures, can be found in the recent article entitled "Improved Access to Supercomputers Boosts Chemical Applications" by Stuart Borman which appeared in the Jul. 17, 1989 edition of *Chemical & Engineering News*, pages 29–32, 35–37. Also, by way of general background, examples of the use of digital computers to predict physical phenomena can be found in such patents as Nackman et al., U.S. Pat. No. 4,797,842, assigned to IBM Corporation, Wolfram, U.S. Pat. No. 4,809,202, assigned to Thinking Machines Corporation, and Konno et al., U.S. Pat. No. 4,819,161, assigned to Hitachi.

Discussions of the leading prior techniques used to determine electronic structures can be found in: D. H. Vanderbilt and S. G. Louie, "Total Energies of Diamond (111) Surface Reconstructions by a Linear Combination of Atomic Orbitals Method," *Phys. Rev. B.*, 30, 6118 (1984); E. R. Davidson, "The Iterative Calculation of a Few of the Lowest Eigenvalues and Corresponding Eigenvectors of Large Real-Symmetric Matrices," *J. Comput. Phys.*, 17, 87, (1975); R. Haydock, "The Recursive Solution of the Schrodinger Equation," *Solid State Physics*, 35, 215 (1980); P. Bendt and A. Zunger, *Solar Energy Research Institute Technical Report TP-202-1698*, (1982); D. M. Wood and A. Zunger, "A New Method for Diagonalising Large Matrices," *J. Phys. A: Math. Gen.*, 18, 1343 (1985); R. Car and M. Parrinello, "Unified Approach for Molecular Dynamics and Density-Functional Theory," *Phys. Rev. Lett.*, 55, 2471 (1985); M. C. Payne, J. D. Joannopoulos, D. C. Allan, M. P. Teter, and D. H. Vanderbilt, "Molecular Dynamics and ab Initio Total Energy Calculations," *Phys. Rev. Lett.*, 56, 2656, (1986); D. C. Allan and M. P. Teter, "Nonlocal Pseudopotentials in Molecular-Dynamical Density-Functional Theory: Application to $SiO_2$," *Phys. Rev. Lett.*, 59, 1136 (1987); and A. Williams and J. Soler, *Bull. Am. Phys. Soc.*, 32, 562 (1987).

II. The Electronic Structure of Hydrogen

To set forth some of the basic concepts of electronic structure determinations, the hydrogen atom, i.e., the simplest material, will be discussed first. The electronic structure of this material can be determined analytically using Schrodinger's equation. In its time-independent, non-relativistic form, Schrodinger's equation is:

$$H\psi = E\psi \qquad (1)$$

where $\psi$ is a quantum mechanical wavefunction, E is the system's energy, and H is the Hamiltonian (energy) operator for the system.

The general Schrodinger's equation of equation 1 is particularized to the problem of the hydrogen atom by the inputting of data from the physical world. Specifically, information regarding the composition of the hydrogen atom is used to formulate the proper Hamiltonian operator for hydrogen. For the hydrogen atom with its one electron and nucleus of one proton, the Hamiltonian becomes:

$$H = (h^2/8\pi^2\mu)\nabla^2 - (e^2/4\pi\epsilon_0)(1/r) \qquad (2)$$

where the first term represents the electron's kinetic energy and the second term represents the electron's potential energy in the electrostatic field produced by the proton. In equation 2, h is Planck's constant ($h = 6.62618 \times 10^{-34}$ Joule-seconds), $\mu$ is the reduced mass of the electron and the proton ($\mu = m_e m_p/(m_e + m_p)$ where $m_e$ is the mass of the electron and $m_p$ is the mass of the proton), $\nabla^2$ is the laplacian operator in, for example, spherical polar coordinates, e is the charge on the electron, and $\epsilon_0$ is the permittivity of free space.

The wavefunctions which solve equation 1 for the Hamiltonian of equation 2 can be written:

$$\psi_{n,l,m}(r,\theta,\phi) = R_{nl}(r)Y_{lm}(\theta,\phi) \qquad (3)$$

where n is the principal quantum number, l the angular momentum quantum number, and m the magnetic or directional quantum number, where $Y_{lm}(\theta,\phi)$ and $R_{nl}(r)$ describe the angular and radial dependence of the wavefunction, $Y_{lm}(\theta,\phi)$ being spherical harmonics in $\theta$ and $\phi$ and $R_{nl}(r)$ being based on the associated Laguerre functions, and where the quantum numbers satisfy the following relationships:

$$n=1,2,\ldots$$

$$0 \leq l \leq n-1$$

$$-l \leq m \leq +l$$

From equation 3, we see that overall electronic structure of hydrogen comprises a set of discrete functions (eigenfunctions) described by the quantum numbers n, l, and m. For each eigenfunction, there is a corresponding discrete value (eigenvalue) for the hydrogen atom's total energy:

$$E = -(\mu e^4 / 8\epsilon_o^2 h^2)(1/n^2) \quad n = 1, 2, \ldots \tag{4}$$

The ground state of hydrogen corresponds to the quantum numbers (1,0,0) and to an energy of:

$$E_o = -\mu e^4 / 8\epsilon_o^2 h^2$$

Equations 3 and 4 along with considerations regarding electron spin have been used to predict various properties of the hydrogen atom. In particular, the spectrum of hydrogen, including the effects of magnetic and electric fields on that spectrum, has been predicted using the wavefunctions of equation 3 and the energy levels of equation 4. With hydrogen as a basis, the spectra of various other atoms, such as helium and the alkali metals, have also been investigated.

In addition, equation 3 forms the basis for the well-known s, p, d, and f orbitals of basic chemistry. Specifically, the s-orbitals are those with l=0, the p-orbitals are those with l=1, the d-orbitals are those with l=2, and the f-orbitals are those with l=3. The graphical representations of these orbitals, i.e., their familiar lobe structures, are obtained from the following relationship between wavefunctions and electron probability densities $\rho(r,\theta,\phi)$, where $\rho(r,\theta,\phi)\cdot\Delta v$ is the probability of finding an electron in a small volume $\Delta v$ centered about a particular set of r, $\theta$, and $\phi$ values:

$$\rho(r,\theta,\phi)=|\psi_{n,l,m}(r,\theta,\phi)|^2 \tag{5}$$

III. Electronic Structures of Complex Materials
A. Introduction

The approach of determining electronic structures by obtaining analytical solutions to Schrodinger's equation, i.e., the approach used for the hydrogen atom, cannot be used for complex materials. Accordingly, a variety of alternate approaches have been developed in the art. The approach used in the present invention is based on the fundamental principle of quantum mechanics that the electronic structure of a system and the system's energy are related by:

$$E = \frac{\int \psi^* E_{op} \psi d^3 r}{\int \psi^* \psi d^3 r} \tag{6}$$

where $E_{op}$ is the energy operator for the system and, as is conventional, the "*" indicates a complex conjugate.

As with the Hamiltonian in Schrodinger's equation, the proper energy operator for a particular system is determined by data from the physical world. Moreover, since equation 6 is used with materials much more complicated than the hydrogen atom, data beyond the composition of the atoms making up the material is necessary to properly formulate the energy operator.

For example, in the case of a crystalline material, the energy operator depends on the lattice structure and spacings, as well as the types of atoms in the crystal and their arrangement. In general, the data includes the geometry and composition of the material whose properties are to be predicted, the material's excitation state, and a description of the environment in which the material resides, e.g., the temperature of the environment, the direction and magnitude of any external forces (pressures) acting on the material, and the direction and magnitude of any electric or magnetic fields imposed upon the material.

B. The Basic Steps of the Procedure

Equation 6 by itself does not give the electronic structure (wavefunction) for the system. However, procedures can be developed whereby starting with equation 6, the electronic structure can be determined. Those procedures rely on: 1) certain properties of the energy; and 2) expanding the wavefunction as a function of a set of "wavefunction" parameters, e.g., as a Fourier-type expansion in plane waves where the coefficients for the various plane waves comprise the wavefunction parameters.

The properties of the energy which are relied on are: 1) for the system's ground state, E must be a minimum; and 2) although there may exist many stationary points in the energy, there are no false minima. Accordingly, the electronic structure of the ground state can be found by looking for values of the parameters which minimize the energy.

The basic steps in finding this minimum are: 1) the selection of a form for the energy operator of equation 6; 2) the selection of an expansion for the wavefunction of the material in terms of wavefunction parameters; and 3) the determination of the values of the wavefunction parameters which minimize the energy expression of equation 6. The improvements provided by the present invention are specifically concerned with step 3 of this three-step process.

1. The Energy Operator

Various forms for the energy operator in equation 6 are known in the art. A typical form and the form which will be used herein for purposes of illustration is:

$$E_{op} = -1/2 \, \nabla^2 + V_{ion}(r) + \\ 1/2 \int \frac{\rho(r')}{|r-r'|} d^3 r' + \epsilon_{xc}(\rho(r)) \tag{7}$$

where the various terms in this expression correspond to the various components of the system's total energy. Specifically, the first term in equation 7 when applied to the wavefunction in the manner prescribed by equation 6 gives the electrons' kinetic energy, the second term $V_{ion}$, referred to in the art as a "pseudopotential", gives the potential energy due to electron/nuclear interactions, the third term gives the potential energy due to Coulombic interactions (repulsions) between the electrons (also known as the Hartree potential), and the fourth term gives the quantum mechanical exchange-correlation potential energy.

In examining equation 7, it is important to note that the Coulombic potential (the third term) and the exchange-correlation potential (the fourth term) both depend on the electron density which in turn depends on the wavefunction (see equation 5). Thus, equation 6 is non-linear in the sense that the wavefunction appears not only outside of the energy operator but also as part of the operator. It is this non-linearity which has made the determination of electronic structures and the predicting of physical and chemical properties based on those structures so difficult and, in many cases, impossible to perform even when supercomputers have been employed.

The details of the derivation of equation 7 can be found in, for example, W. Kohn and L. J. Sham, *Phys. Rev.*, 140, A1133 (1965). The primary theoretical foundations underlying this form for the energy operator are:

(a) The fact that the ground state of any system of electrons and nuclei is uniquely defined by its electron density function $\rho(r,\theta,\phi)$. See P. Hohenberg and W. Kohn, *Phys. Rev.*, 136, B864 (1964). (Note that Hohenberg and Kohn also proved that the correct ground state electron density for a system is the one which minimizes the total energy of the system.) Accordingly, to predict physical properties all that is needed is the wavefunctions for the electrons, not for both the electrons and the nuclei. Thus, the energy operator of equation 7 is written only in terms of the energies (kinetic and potential) of the electrons and the wavefunctions which are determined are the wavefunctions of the electrons.

(b) The independent particle theory applied to electrons under which each electron is assumed to see the other electrons as an average rather than individually. This theory requires that the total wavefunction be an anti-symmetric product of single particle wavefunctions. The single particle wavefunctions must be linearly independent and can be assumed to be orthogonal. This orthogonality condition is used below.

(c) The local density approximation (LDA) under which it is assumed that the exchange-correlation energy on a point by point basis is a function of the electron density and is given by the same expression as would exist in a homogeneous electron gas.

(d) The approximation that the electron/nuclear interactions can be represented by pseudopotentials. See G. B. Bachelet, H. S. Greenside, G. A. Baraff and M. Schluter, *Phys. Rev. B*, 24, 4745 (1981). The pseudopotentials can be either "local" or "non-local" depending upon whether angular momentum effects are to be included in the approximation. Also, where needed, relativistic effects can be included in the pseudopotentials. Such effects are generally not of particular importance for atoms lighter than neon. For sodium through argon, the effects become moderately important, and from potassium through krypton, they become even more important. Above krypton, relativistic effects need to be included in the determination of the pseudopotentials. In general, it is preferred to include relativistic effects in the calculation of all pseudopotentials since this leads to more accurate wavefunctions and thus more accurate predictions of physical and chemical properties. When relativistic effects are included, the relativistic Schrodinger's equation, as opposed to the non-relativistic equation, is used in calculating the pseudopotentials.

(e) The assumption that the electrons of the material respond adiabatically to any change in the location of the material's nuclei. Accordingly, the electrons are assumed to be in steady state and the energy operator of equation 7 is time independent.

As is evident, Equation 7 is a general equation applicable to all types of materials. To be used to predict the physical properties of a specific material, this equation must be written specifically for that material. This is done by inputting physical data into equation 7 regarding the material of interest. In particular, the pseudopotentials of the second term of equation 7 depend upon the types and locations of the atoms making up the material and upon the electronic structure of those atoms, including, for example, the numbers of valence and non-valence electrons which each atom has. Data of this type is thus required before the wavefunction for the electrons of a specific material can be determined.

2. The Wavefunction Expansion

As with the energy operator of equation 7, various expansions for the wavefunction describing the electrons of a material are known in the art. A typical expansion and the expansion which will be used herein for purposes of illustration is a set of n orthogonal bands $\psi_n(r)$, each band being occupied by two of the material's valence electrons and each band being expressed as a linear combination of plane waves:

$$\psi_n(r) = \sum_G C_{Gn} e^{i2\pi f(r)} \qquad (8)$$

where $$f(r) = \vec{G} \cdot \vec{r}$$

and where the $\vec{G}$'s are vectors, namely, reciprocal lattice vectors, whose directions depend on the lattice geometry of the material whose properties are to be predicted. Specifically, for a material having a unit cell whose sides are the vectors $l_1$, $l_2$, and $l_3$, the $\vec{G}$'s satisfy the relationship $$\vec{G} \cdot \vec{l} = n_i$$

where $n_i$ is an integer.

The unknown "wavefunction" parameters in equation 8 are the $C_{Gn}$'s. The number of plane waves and thus the number of $C_{Gn}$'s needed in the expansion depends upon the number and types of atoms in the material's unit cell. For example, for silicon atoms, on the order of 50–100 plane waves are needed per atom, while for oxygen atoms, a greater number on the order of 500–1,000 is required. Accordingly, for an 8-atom silicon unit cell, on the order of 200–800 plane waves would be needed per band, while for a 12-atom unit cell of $SiO_2$ containing 4 silicon atoms and 8 oxygen atoms, the number grows to 4,000–8,000 plane waves per band.

The number of bands required for a particular material depends upon the number of valence electrons. For example, silicon has 4 valence electrons, while oxygen has 6. Accordingly, for a unit cell having 8 silicon atoms, 16 doubly-occupied bands would be required, while for a 12-atom $SiO_2$ unit cell, the number grows to 32 bands ($\frac{1}{2}(4\times4\;(Si)+8\times6\;(O))$).

The magnitude of the problem thus becomes apparent. To determine the electronic structure of silicon, on the order of 10,000 $C_{Gn}$'s need to be determined, while for silica ($SiO_2$), the number grows to between a hundred thousand and a quarter of a million parameters. It is these large numbers, in combination with the non-linearity of equation 6 discussed above, which make the determination of wavefunctions for complex materials so formidable.

As with any expansion, the expansion of equation 8 embodies certain assumptions regarding the material whose physical or chemical properties are to be determined. In particular, the use of a plane wave expansion assumes that the wavefunction satisfies periodic boundary conditions, i.e., it is assumed that the structure of the material of interest repeats at regular intervals or can be approximated by a repeating structure.

Also, for simplicity, "k-points" have not been explicitly included in equation 8, i.e., equation 8 has been written for $\vec{k}=0$. In practice, k-points other than $\vec{k}=0$ are used so as to incorporate into the wavefunction periodic behavior extending beyond a single unit cell of the material. Typically, at least 4 k-points are employed, and a separate set of $C_{Gn}$'s are determined for each k-point. Thus, in practice, the numbers of $C_{Gn}$'s which need to be determined are at least four times greater than the values given above, e.g., for a material like silica, on the order of 0.5–1.0 million $C_{Gn}$'s must be determined.

3. Methods for Determining the Wavefunction Parameters

As discussed above (see Section III.B), the desired values for the $C_{Gn}$'s are not obtained directly from equation 6. Rather, they are obtained by systematically searching for values of the $C_{Gn}$'s for which the energy as expressed by equation 6 has its minimum value.

The search is performed using the gradient of the energy with respect to the $C_{Gn}$'s (hereinafter referred to simply as the "gradient"). The gradient, or, more accurately, the negative of the gradient points in the direction of decreasing energy. Accordingly, using the gradient, a systematic search can be made for the set of $C_{Gn}$'s which minimize the energy.

In particular, the search can be made by: 1) selecting a set of trial values for the $C_{Gn}$'s, 2) evaluating the gradient for the trial values, 3) determining a set of changes to the trial values using the evaluated gradient, 4) constructing a revised set of trial values by combining a portion of the changes with a portion of the original trial values, and 5) repeating (iterating) the process until convergence is reached.

As one example of steps 3 and 4, the set of changes to the trial values can be simply the components of the gradient and the revised set of trial values can be constructed by simply adding to each of the original $C_{Gn}$ values a portion of the component of the gradient for that $C_{Gn}$, the portion being the same for all of the $C_{Gn}$'s and being chosen to be small enough so that the iterative process does not become unstable. This method is known in the art as the "method of steepest descents" and is one of the methods employed below in the examples.

Of course the success of using an iterative approach to find the $C_{Gn}$'s depends upon the number of iterations which must be performed before convergence is reached. As discussed above, the number of $C_{Gn}$'s can often be on the order of a million or more, and a set of $C_{Gn}$'s needs to be determined for each complete iteration. Accordingly, it is of prime importance to achieve convergence in as few iterations as possible. The improvements provided by the present invention are directed to reducing the number of iterations needed to find the $C_{Gn}$'s.

Increases in the number of iterations needed to achieve convergence can come from various sources, including 1) the characteristics of the gradient, 2) the method used to determine the set of changes to the trial values at each iteration (i.e., step 3 above), and 3) the way in which the changes and the original values are combined to produce the revised set of $C_{Gn}$'s at each iteration (i.e., step 4 above).

For example, in connection with the invention, it was determined that numerous iterations are wasted in dealing with the components of the gradient corresponding to large $\vec{G}$'s, i.e., in dealing with the components of the gradient corresponding to plane waves having a high spatial frequency. These components of the gradient have a larger magnitude than other components and thus tend to limit the magnitude of the changes to the trial values which can be made at any one iteration without jeopardizing the stability of the process. As discussed fully below, in accordance with certain aspects of the invention, this source of iteration growth is dealt with by "conditioning" the gradient in particular ways before it is used to determine the set of changes.

Similarly, it was found that the steepest descents method is not the most effective method for determining the set of changes to the trial values. Rather, as discussed fully below, the method known as the "conjugate gradient method" was found to be significantly more efficient in terms of number of iterations needed to achieve convergence. A discussion of the conjugate gradient method can be found in M. R. Hestenes and E. Stiefel, "Methods of Conjugate Gradients for Solving Linear System," *J. Res. Nat. Bur. Stand.*, 49, 409, (1952), and in I. Stich, R. Car, M. Parrinello, and S. Baroni, "Conjugate Gradient Minimization of the Energy Functional: A New Method for Electronic Structure Calculation," *Phys. Rev. B.*, 39, 4997, (1989).

Finally, it was found that a major reduction in the number of iterations can be achieved by parameterizing the energy in the region of the trial values and using the parameterization to determine the portion of the changes and the portion of the original $C_{Gn}$ values which should be combined to produce the revised set of trial values. More particularly, the parameterization is used to find the portion of the changes and the portion of the original values which when added together minimize the energy to second order in the region of the original values. In this way, the reduction in energy per iteration is maximized, i.e., each iteration is made as effective as possible. By so doing, the total number of iterations needed to complete the determination of the $C_{Gn}$'s is significantly reduced.

DESCRIPTION OF THE INVENTION

In view of the foregoing, it is an object of the present invention to provide apparatus and methods for determining the electronic structure of materials and, in particular, complex materials. It is a further object of the invention to provide apparatus and methods for predicting physical and chemical properties of materials from their electronic structures. It is an additional object of the invention to provide apparatus and methods for 1) predicting materials having selected physical or chemical properties under selected conditions and 2) preparing the materials so predicted.

The objects of the invention also include providing apparatus and methods for iteratively determining values for the wavefunction parameters of a wavefunction expansion, e.g., a plane wave expansion. More particularly, it is an object of the invention to provide apparatus and methods which reduce the number of iterations needed to determine such parameters.

To achieve the foregoing and other objects, the invention in accordance with certain of its aspects provides apparatus and methods for parameterizing the energy (E) of the electrons of a material in the region of a set of values for the wavefunction parameters of the material (e.g., in the region of a set of values for the $C_{Gn}$'s).

By means of this parameterization, the process of finding the values of the wavefunction parameters which minimize the energy is optimized in the sense that for each iteration, the "optimum" amount of change to the current set of values is made. More particularly, for a current set of wavefunction parameters $\vec{C}^i$ and a set of changes to those parameters $\vec{D}^i$, where "i" is the number of current iteration, the parameterization allows one to select a portion of the $\vec{C}^i$ and a portion of the $\vec{D}^i$ which when combined with each other, minimize the energy. The next set of values for the wavefunction parameters ($\vec{C}^{i+1}$) then becomes the combination of the selected portions. Since the overall goal is to minimize the energy, this approach plainly makes the maximum use of each set of $\vec{D}^i$.

In certain preferred embodiments, the portions of the $\vec{C}^i$ and the $\vec{D}^i$ are given by:

$$\vec{C}^{i+1} = \vec{C}^i \cos\theta + \vec{D}^i \sin\theta \tag{9}$$

and the parameterization is of the form:

$$E(\theta) = E_{avg} + E_{c1} \cos 2\theta + E_{s1} \sin 2\theta \tag{10}$$

where $\theta$ is a parameter or variable (also referred to as an "energy parameterization variable") and $E_{avg}$, $E_{c1}$, and $E_{s1}$ are coefficients (also referred to as "energy parameters") whose values must be determined before the parameterization can be used to optimize the iteration.

Since there are three coefficients, three pieces of information are needed to obtain values for $E_{avg}$, $E_{c1}$, and $E_{s1}$. For example, if one knew three values of E, e.g., for $\theta=0°$, $45°$, and $90°$, then one could write equation 10 three times, once for each of three values, and then solve the three equations for the three unknown coefficients. As discussed fully below, a better choice for the three pieces of information is the energy at $\theta$ equal to zero, the energy at $\theta$ equal to a small angle such as $\pi/300$, and the partial derivative of the energy with respect to $\theta$ evaluated at $\theta=0$. (More particularly, only the portion of the energy which depends on $\theta$, i.e., on the changes $\vec{D}^i$, need be evaluated since the remainder of the energy is an additive constant which does not affect the minimization process.) The three equations in the unknowns $E_{avg}$, $E_{c1}$, and $E_{s1}$ then become:

$$E(0) = E_{avg} + E_{c1} \tag{11}$$
$$E(\pi/300) = E_{avg} + 0.99978 E_{c1} + 0.02094 E_{s1}$$
$$\left. \frac{\partial E(\theta)}{\partial \theta} \right|_{\theta=0} = 2 E_{s1}$$

As discussed below, using equation 6, the left hand sides of these equations can be written in terms of $\vec{C}^i$ and $\vec{D}^i$. Since $\vec{C}^i$ is known at the beginning of the ith iteration and since $\vec{D}^i$ is determined as part of the ith iteration, equations 11 can be solved for $E_{avg}$, $E_{c1}$, and $E_{s1}$. With these values known, the value of $\theta$ which minimizes equation 10 can be determined. Specifically, the values of $\theta$ for which $E(\theta)$ is an extremum are given by:

$$\theta = 1/2 \tan^{-1} \frac{E_{s1}}{E_{c1}} \tag{12}$$

This equation has two roots in the region between 0 and $\pi$. The root which minimizes the energy, i.e., $\theta_{min}$, is obtained by evaluating equation 10 for each of the roots and selecting the root which produces the lower energy.

Finally, with $\theta_{min}$ determined, $\vec{C}_{i+1}$ is determined from equation 9.

In considering the foregoing it is important to note that there are two separate parameterizations at work: one for the wavefunction using wavefunction parameters such as the $C_{Gn}$'s, and one for the energy using an energy parameterization variable such as $\theta$. The ultimate goal is to obtain values for the wavefunction parameters; the energy parameterization variable is employed as part of the process and serves to minimize the number of iterations needed to obtain the values for the wavefunction parameters.

In accordance with another of its aspects, the invention provides apparatus and methods for conditioning the gradient (also referred to herein as "preconditioning the gradient") before it is used to determine the set of changes ($\vec{D}^i$) to the set of wavefunction parameters ($\vec{C}^i$). As discussed above, it has been found that the gradient is dominated by components corresponding to plane waves having a high spatial frequency and that the presence of these components in the gradient results in wasted iterations, i.e., iterations which do produce a changed set of wavefunction parameters but which do not produce substantial movement towards the energy minimum.

Accordingly, in accordance with the invention, the values of these high spatial frequency components are reduced relative to the values of components having lower spatial frequencies. Specifically, this reduction is accomplished by multiplying each component of the gradient by a function (f(x)) of the ratio (x) of 1) the kinetic energy $E_{kin}(\vec{G})$ of the plane wave corresponding to that component, to 2) the kinetic energy expectation value ($E_{kin}$) for all of the plane waves being iterated, i.e.

$$x = E_{kin}(\vec{G})/E_{kin} \tag{13}$$

For a plane wave having a spatial frequency $\vec{G}$, $E_{kin}(\vec{G})$ is given by:

$$E_{kin}(\vec{G}) = 2\pi^2 (\vec{G})^2 \tag{14}$$

and $E_{kin}$ is given by:

$$E_{kin} = \sum_G C_G^{i*} \cdot C_G^i E_{kin}(\vec{G}) \tag{15}$$

where $C_G^i$ is the value of the wavefunction parameter for the Gth plane wave at the beginning of the ith iteration. Note that for k-points other than $\vec{k}=0$, the kinetic energy of the Gth plane wave is given by:

$$E_{kin}(\vec{G}) = 2\pi^2 (\vec{k} + \vec{G})^2$$

Preferably, the function of x used to multiply the gradient components has a value of 1.0 as becomes $\vec{G}$ small and has a value which approaches $1/(\vec{G})^2$ or more particularly $$1/(2(E_{kin}(\vec{G})-E_{kin}))$$

as $\vec{G}$ becomes large. For example, the function can be a ratio of two polynomials in x wherein the polynomial of the numerator of the ratio is of lower order than the polynomial of the denominator. A particularly preferred polynomial of this type is:

$$f(x) = \frac{27 + 18x + 12x^2 + 8x^3}{27 + 18x + 12x^2 + 8x^3 + 16x^4} \quad (16)$$

In accordance with a further aspect of the invention, the conjugate gradient method is used to determine the set of changes ($\vec{D}^i$) to the current set of wavefunction parameters ($\vec{C}^i$). This method adjusts the gradient for the ith iteration by combining with it portions of the changes made during prior iterations. In this way, the method constrains the iterative process from seeking the energy minimum along old directions already dealt with in prior iterations.

In accordance with certain preferred embodiments of the invention, the iterative technique is applied a band at a time rather than to all the bands simultaneously. That is, the $C_{Gn}$'s for one band are iterated a number of times with the $C_{Gn}$'s for the other bands being held constant. After this process has been applied to all the bands, the set of bands is preferably transformed (reordered) by a similarity transformation before the process of iterating individual bands is repeated. The entire process of iterating the individual bands and then reordering is continued until a set of $C_{Gn}$'s for all the bands is found which is self-consistent.

Preferably, all of the foregoing aspects of the invention are used together, although if desired, individual aspects can be used separately. When all aspects are used together, increases in rates of convergence of at least an order of magnitude are achieved in comparison with existing methods for determining wavefunction parameters and, in some cases, increases on the order of a thousand fold are achieved.

For example, in terms of computer time, a wavefunction determination which with prior techniques would have taken on the order of 20 hours on a supercomputer, e.g., a Cray XMP supercomputer, only takes on the order of 1 hour with the present invention using the same equipment. This significant reduction in computer time means that: 1) wavefunction determinations which previously could not be performed because they took too long can now be performed; and 2) wavefunction determinations which previously could only be performed on a supercomputer can now be performed on more widely available equipment such as on work stations. These results, made possible by the present invention, open up new frontiers in the use of electronic structures to understand the behavior and properties of complex materials.

In addition to the foregoing aspects, the invention also provides methods for 1) predicting physical and chemical properties of materials and 2) preparing materials having selected physical properties. It is in these areas that the reduced computer time achieved by the invention is of particular importance.

As is known in the art, the predicting of physical and chemical properties from electronic structures often involves determining multiple electronic structures. An example will illustrate the approach. Consider the problem of predicting the lattice constant for the diamond structure of silicon. This problem can be solved by the steps of: 1) determining electronic structures for a set of "reasonable" lattice constants; 2) calculating the ground state energy for the system for each of the electronic structures; 3) plotting the ground state energy versus the set of lattice constants; and 4) interpolating the data to select the lattice constant which produces the minimum ground state energy, the interpolated lattice constant being the predicted lattice constant for the material.

Clearly, the more data points which can be used, the better will be the predicted lattice constant. Since an electronic structure must be determined for each lattice constant tested, the need for apparatus and methods for determining such structures rapidly is evident.

Techniques similar to the lattice constant technique can be used for numerous other physical and chemical properties including, among others, compressibility, polarizability, ability to exhibit the piezoelectric effect, surface reactivity, and the like. In each case, multiple electronic structures are determined thus making the ability to determine such structures rapidly of critical importance.

Along these same lines, for many materials, the exact locations of the atoms making up the material's unit cell will not be known at the beginning of the electronic structure determination process. For these materials, a reasonable set of atomic locations is assumed, an electronic structure is determined for the assumed locations, the forces on the atoms (specifically, the Hellman-Feynman forces) are determined from the electronic structure, the locations of the atoms are changed (relaxed) based on the forces, and the process is repeated until a stable set of locations for the atoms is found. Again, this process requires multiple determinations of electronic structures and thus requires an efficient technique for determining such structures.

Although the prediction of many physical and/or chemical properties requires the determination of multiple electronic structures, some properties can be predicted directly from a single set of wavefunction parameters. For example, the optical absorption and chemical bonding of materials can be predicted in this way. For these types of predictions, the ability of the invention to handle large numbers of bands and large numbers of plane waves makes for more accurate predictions and in some cases, allows predictions to be made which previously were not possible. Because of the capabilities of the present invention, its error range in making predictions is generally on the order of 1–2% or less.

One of the most important properties which can be predicted from the determination of a set of wavefunction parameters for a material is the material's three-dimensional configuration, i.e., where the atoms making up the material are located in space. For this property, as well as other properties, an important aspect of the invention is the displaying of the property in a form which can be easily interpreted by scientists, engineers, and others who wish to use or study the material. In the case of three-dimensional configurations, the display can be conveniently made using a graphics terminal or plotter and appropriate graphics software. Such displays are of particular importance in connection with pharmaceutical applications of the invention since as is well known, the activity of many biological materials depends upon their secondary and tertiary structures.

In addition to predicting physical and chemical properties from electronic structures, the present invention provides methods for preparing materials having desired properties. These aspects of the invention involve the following steps:

(1) selecting a trial material, e.g., selecting the atomic composition, atomic positions, and excitation state of a material which might reasonably have the desired physical or chemical property;

(2) selecting trial environmental conditions under which the material is to have the desired property, e.g., selecting the temperature, pressure, and/or electromagnetic environment under which the material is to have the property;

(3) determining a wavefunction for the electrons of the trial material under the trial environmental conditions using the methods and apparatus described above;

(4) predicting a physical or chemical property of the trial material from the wavefunction;

(5) changing the trial material and/or the trial environmental conditions and repeating steps (3) and (4) until the predicted property is the desired property; and (6) preparing the trial material selected in step (5).

It should be noted that in this process, the trial material need not be the final material which is to be sold or used and the trial environmental conditions need not be the final environmental conditions under which the final material operates. Rather, the trial material and/or the trial environmental conditions can be an intermediate material and/or an intermediate environmental condition which forms a part of the process for producing the final material.

For example, the trial material can be a chemical intermediate, catalyst, or similar substance which is formed during or used in the process of producing a final material, and the wavefunction determination can be used to select such a substance and/or to find environmental conditions which enhance the production, activity, or other characteristics of interest of the substance.

Along these lines, steps 1–6 of the above process can be used to optimize entire manufacturing processes by identifying reaction conditions and/or material compositions which enhance the properties and/or yield of a finished product. Prior to the present invention, such optimizations were generally not performed because of the large amounts of computer time required to determine even one set of wavefunction parameters. With the enhanced convergence rates achieved by the invention, such multi-step optimization procedures are now possible.

The preparation of the trial material in accordance with step (6) of the above process will depend upon the particular technology to which the process has been applied. For example, in the case of new types of glass materials, glass forming technology is used. Similarly, in the case of materials which are to have biological applications, procedures for preparing pharmaceutical preparations are used. Discussions of techniques for synthesizing materials in these as well as other arts to which the invention may be applied, can be found in the scientific and patent literature relating to the art, which literature is readily available to those skilled in the art.

The accompanying drawings, which are incorporated in and constitute part of the specification, illustrate the preferred embodiments of the invention, and together with the description, serve to explain the principles of the invention. It is to be understood, of course, that both the drawings and the description are explanatory only and are not restrictive of the invention.

DESCRIPTION OF THE PREFERRED EMBODIMENTS

Figure 1A:
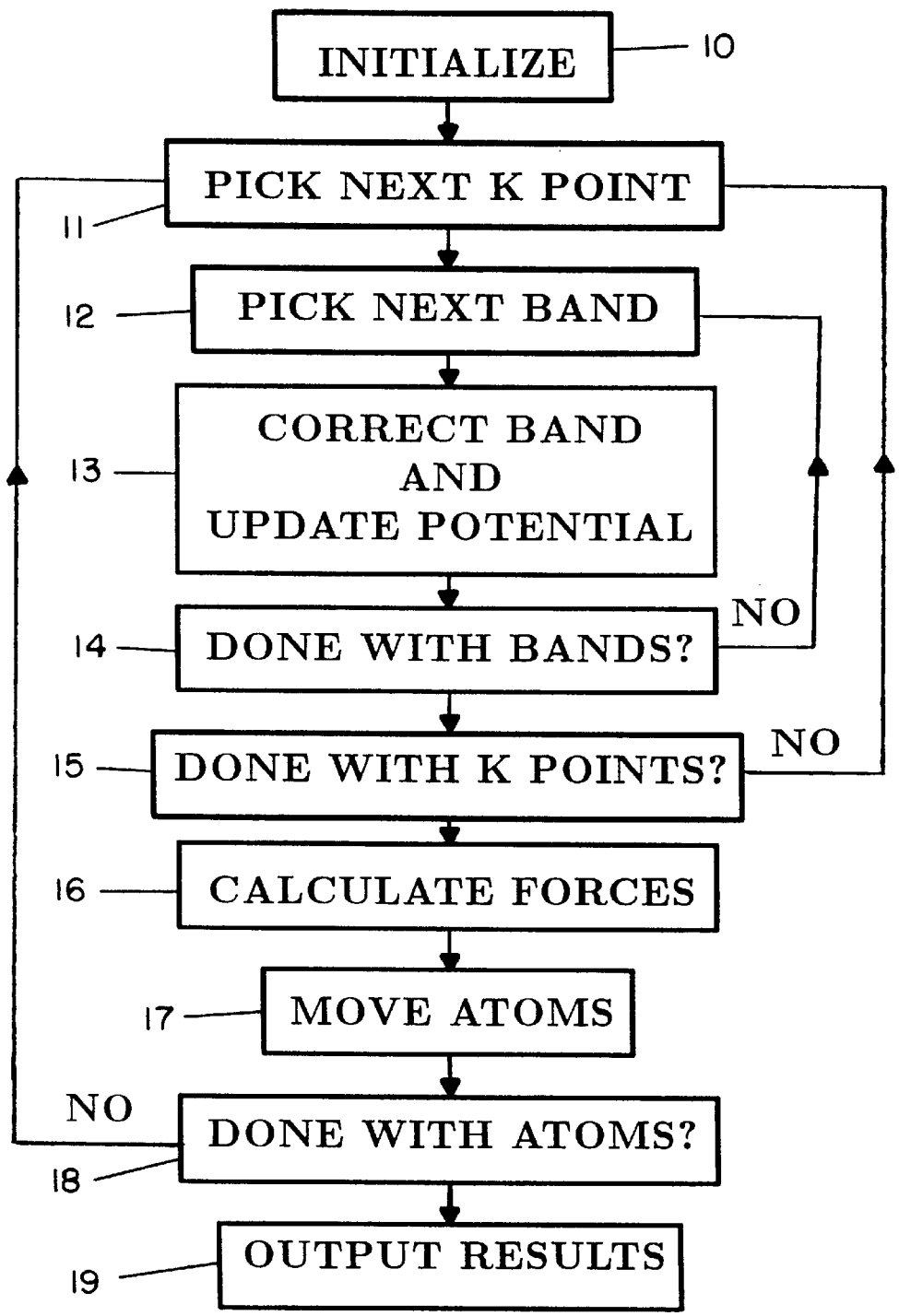
FIGS. 1A and 1B show a flow diagram of a computer program for implementing the present invention on, for example, a supercomputer or a work station.

As discussed above, the present invention provides apparatus and methods for finding values for the $C_{Gn}$'s of equation 8 which minimize the energy expression of equation 6. In outline the steps of the method are:

(I) Selecting starting values for the $C_{Gn}$'s for all of the bands of the material, e.g., all 32 bands in the case of silica.

(II) Improving the starting values for the bands on a band-by-band basis while holding constant the values of the $C_{Gn}$'s for the bands not being improved, by iteratively:

(A) determining the gradient of the energy with respect to the $C_{Gn}$'s of the band being improved;

(B) preconditioning the components of the gradient;

(C) applying the conjugate gradient technique to the preconditioned components of the gradient to determine a set of changes to the $C_{Gn}$'s of the band being improved; and (D) applying the energy parameterization technique to the original set of values for the $C_{Gn}$'s and to the set of changes to determine improved values for the $C_{Gn}$'s for the band being improved.

(III) Reordering the bands.

(IV) Repeating steps II and III until the values for all of the $C_{Gn}$'s converge.

The apparatus of the invention comprises a digital computer system configured by suitable programming to perform the foregoing steps. The programming can be done in various programming languages known in the art. A preferred programming language is the FORTRAN language which is particularly well-suited to iterative techniques employing double precision calculations. Other languages which can be used include BASIC, PASCAL, C, $C^{++}$, and the like.

The computer system can comprise a supercomputer and its associated peripherals such as the supercomputers and peripherals currently being manufactured by Cray Research, Fujitsu, NEC, and Hitachi. For some problems, a work station computer such as those manufactured by, among others, IBM, Sun, Digital Equipment, Hewlett Packard, Stellar, and Ardent will be sufficient.

Preferably, the processing portion of the computer system should have the following characteristics: a processing rate of at least 10 million instructions per second; a word length of at least 32 bits so that the double precision word length is at least 64 bits, at least 16 megabytes of memory, and at least a few hundred megabytes of disk storage. The system should include means for inputting data regarding the atomic composition, atomic positions, and excitation state of the material whose wavefunction is to be determined, as well as data regarding the environment in which the material resides. Suitable inputting means include disk drives, tape readers, keyboards, and the like.

Similarly, the computer system should include means for displaying the results of the wavefunction determinations, including the results of predictions of physical and/or chemical properties of the material whose wavefunction has been determined. Suitable display means include CRT's, printers, graphics plotters, and the like. Alternatively, the results of wavefunction determinations/predictions can be outputted to a disk drive, tape drive, or the like for further processing and/or subsequent display.

With the foregoing general discussion as a background, the various elements of the method and apparatus of the invention will now be discussed individually. In this discussion, the $C_{Gn}$'s of a particular band, e.g., the mth band, will be treated as a vector $\vec{C}_m$, where the components of the vector are the $C_{Gn}$'s for the band. The value of the $\vec{C}_m$ vector at the beginning of an iteration will be represented by $\vec{C}_m^i$ and at the end of an iteration by $\vec{C}_m^{i+1}$. The values of all of the $C_{Gn}$'s at any point in the process will be referred to as the "trial vectors" at that point, i.e., the set of all the $\vec{C}_m$'s at that point.

I. The Selection of Starting Values for the Wavefunction Parameters

The first step in finding the values of the $C_{Gn}$'s which minimize the energy is to select a set of starting values for the parameters. In general, any set of starting values for the $C_{Gn}$'s, i.e., any set of $\vec{C}_m^0$ vectors, can be used provided that the starting set is not orthogonal to the ground state (lowest energy state) which is being sought.

In the examples presented below, the starting vectors were filled with random numbers and then orthonormalized, i.e., made orthogonal to one another and normalized so that the magnitude of each vector was 1.0. The orthogonality condition is a result of the antisymmetry property of electrons discussed above (see section III.B.1 of the Description of the Technology); the normalization condition is a convenient way to deal with the denominator of equation 6. As will be seen below, the $\vec{C}_m$'s are required to satisfy these two conditions at all stages of the process.

Starting vectors generated from random numbers were used in the examples to demonstrate the robustness of the process. Also, the use of random numbers made it unlikely that the starting vectors would be orthogonal to the ground state. Other starting vectors can be used and in general are used to take advantage of available knowledge regarding the ground state wavefunction of the material of interest.

II. The Improvement of the Values of the Wavefunction Parameters

Once the starting values for the $C_{Gn}$'s have been selected, the values are improved on a band-by-band basis by iteratively applying the steps of: (A) determining the gradient, (B) preconditioning the gradient, (C) applying the conjugate gradient technique, and (D) applying the energy parameterization technique. Each of these steps is discussed separately below. For purposes of illustration, the steps are discussed in terms of the transition from the (i)th to the (i+1)th iteration of the mth band.

A. The Determination of the Gradient

The first step in improving the values of the wavefunction parameters for the mth band is to determine the components of the gradient of the energy with respect to those parameters. As is known in the art, those components can be obtained using the Hamiltonian matrix H whose elements are defined by:

$$H_{ij} = \int e^{-i2\pi A(i)} H_{op} e^{i2\pi A(j)} d^3 r \quad (17)$$

where $$A(i) = \vec{G}_i \cdot \vec{r}$$
$$A(j) = \vec{G}_j \cdot \vec{r}$$
$$H_{op} = -1/2 \nabla^2 + V_{ion}(r) + \mu_{xc}(r) + \int \frac{\rho(r')}{|r-r'|} d^3 r' \quad (18)$$

and $$\mu_{xc}(r) = \epsilon_{xc}(r) + \rho(r) \partial \epsilon_{xc}(r)/\partial \rho(r)$$

and where $V_{ion}(r)$, $\epsilon_{xc}(r)$ and $\rho(r)$ have the meanings discussed above in connection with the energy operator of equation 7. Note that, as with the energy operator, the Hamilton operator $H_{op}$ of equation 18 is a non-linear operator in the sense that it depends upon the electron probability density $\rho(r)$ which in turn depends upon the $C_{Gn}$'s which are to be determined. Thus, the elements of the Hamiltonian matrix are continually changing during the iterative process as $\vec{C}_m$ changes.

In terms of the Hamiltonian matrix, the unconstrained gradient of the energy with respect to the components of $\vec{C}_m^i$ is given to within a multiplicative constant by:

$$\nabla E = H \cdot \vec{C}_m^i \quad (19)$$

The product on the right hand side of equation 19 is preferably evaluated with the use of Fourier transforms. Specifically, the Hamiltonian matrix can be split into parts which are diagonal either in Fourier space or in real space. Consequently, the entire Hamiltonian matrix need never be stored.

In particular, the kinetic energy operator ($-\frac{1}{2}\nabla^2$) is diagonal in momentum (Fourier) space, while the potential energy operator (i.e., the remainder of the Hamiltonian operator) is diagonal in real space. Accordingly, the product of equation 19 can be formed by multiplying the potential evaluated on a grid in real space by the values of the single particle wavefunction on the same grid. These values are obtained by Fourier transforming $\vec{C}_m^i$. The result of this operation is Fourier transformed into momentum space where it is combined with the contribution from the kinetic energy operator. Fast Fourier transforms (FFT) are preferably employed in making these transformations. A particularly preferred form of FFT is the mixed-radix form which allows the number of grid points in a single dimension to be divisible by numbers other than 2. In particular, the number of grid points in one dimension will typically contain factors of 2, 3, and 5.

The gradient generated by operating on the vector $\vec{C}_m^i$ with the matrix H will in general include a portion which is parallel to $\vec{C}_m^i$. Because of the normalization requirement, that portion can have no net effect on the iterative procedure since moving in the direction of $\vec{C}_m^i$ will simply change the length of $\vec{C}_m$ and any such change in length will automatically be removed at subsequent stages of the process by the requirement that $\vec{C}_m \cdot \vec{C}_m$ must end up equal to 1.

Accordingly, it is convenient to subtract from the gradient that portion of the gradient which is parallel to $\vec{C}_m{}^i$. The magnitude ($\lambda_m{}^i$) of the portion parallel to $\vec{C}_m{}^i$ is given by the dot product of $\vec{C}_m{}^i$ with the gradient:

$$\lambda_m{}^i = \vec{C}_m{}^{i \cdot} (H \cdot \vec{C}_m{}^i)$$

Accordingly, the portion of the gradient not parallel to $\vec{C}_m{}^i$ (referred to in the art as the "residual" or the "residual vector") is given by:

$$\vec{R}^i = -(H \cdot \vec{C}_m{}^i - \lambda_m{}^i \vec{C}_m{}^i) \quad (20)$$

where the negative sign has been added since the direction in which $\vec{C}_m{}^i$ is to be changed is along the negative of the gradient. Similarly, no gain in the total energy can result from changes parallel to other bands, and thus these components are also subtracted from the residual vector.

B. The Preconditioning of the Gradient

With the gradient or, more specifically, the residual in hand, the next step is to precondition the gradient (residual) to lessen the effects of the components of the gradient corresponding to high spatial frequencies (large $\vec{G}$'s). The preconditioning is performed by multiplying the residual by a conditioning matrix defined by:

$$K_{GG'} = \delta_{GG'} f(x)$$

where x and f(x) are given by equations 13 and 16 above and $\delta_{GG'}$ is the Kronecker delta which has a value of 1 when $G = G'$ and a value of 0 when $G \neq G'$.

The preconditioned residual $\vec{R}'^i$ thus becomes:

$$\vec{R}'^i = \vec{R}^i \cdot K$$

In general, the preconditioned residual vector will include components parallel to the $\vec{C}$ vectors for bands other than the mth band, as well as components parallel to $\vec{C}_m{}^i$ which were reintroduced into the residual by the conditioning matrix. The energy parameterization technique discussed below uses a set of changes to the $\vec{C}_m{}^i$ vector which are orthogonal to all of the bands. Accordingly, the final gradient-dependent vector ("$\vec{G}$" vector) which is passed to the conjugate gradient technique is obtained by subtracting from the preconditioned residual vector the components of that vector which are parallel to the $\vec{C}$ vectors. Specifically, $\vec{G}^i$ is given by:

$$\vec{G}^i = \vec{R}'^i - \sum \alpha_{mk}^i \vec{C}_k - \alpha_{mm}^i \vec{C}_m^i$$

where the summation is for $k \neq m$ and where $$\alpha_{mk}^i = \vec{C}_k^* \cdot \vec{R}'^i$$

C. The Application of the Conjugate Gradient Technique

As discussed above, the conjugate gradient method adjusts the gradient for the ith iteration (more particularly, the gradient-dependent vector $\vec{G}^i$) by combining with it portions of the changes made during prior iterations. In this way, the method constrains the iterative process from seeking the energy minimum along old directions already dealt with in prior iterations.

More specifically, the conjugate gradient technique defines the direction along which the total energy is to be minimized as:

$$\vec{F}^i = \vec{G}^i + \gamma^i \vec{F}^{i-1}$$

where $$\gamma^i = (\vec{G}^{i*} \cdot \vec{G}^i)/(\vec{G}^{i-1*} \cdot \vec{G}^{i-1})$$

if preconditioning is not used, or $$\gamma^i = (\vec{G}^{i*} \cdot \vec{R}^i)/(\vec{G}^{i-1*} \cdot \vec{R}^{i-1})$$

if preconditioning is used, and where $$\gamma^1 = 0$$

in both cases.

The addition of some of the previous vector $\vec{F}^{i-1}$ to $\vec{G}^i$ will in general result in a vector having a component parallel to $$\vec{C}_m^i.$$

As discussed above, such a component cannot have any lasting effect because of the normalization requirement. Accordingly, before proceeding to the energy parameterization procedure, it is convenient to form a further vector—the vector of changes $\vec{D}$—which is obtained by projecting the band vector $$\vec{C}_m^i$$

from $\vec{F}^i$ and normalizing. This new vector $\vec{D}^i$ is passed to the energy parameterization procedure, while $\vec{F}^i$ is saved and used along with $\vec{G}^{i+1}$ to generate $\vec{F}^{i+1}$.

D. The Application of the Energy Parameterization Technique

As discussed above, the energy parameterization technique involves selecting those portions of the $\vec{C}^i$ and $\vec{D}^i$ vectors which when combined together to produce $\vec{C}_m^{i+1}$ minimize the energy in the region of $\vec{C}_m^i$.

The portions to be combined are given by equations 9 through 12 above. The values of $E(0)$, $E(\pi/300)$, and of the partial derivative of $E(\theta)$ with respect to $\theta$ evaluated at $\theta = 0$ are obtained as follows.

As stated above, the only part of the total energy which must be evaluated is that part which depends on $\theta$. This includes the Hartree energy (i.e., the energy corresponding to the third term in equation 7), the exchange-correlation energy (i.e., the energy corresponding to the fourth term in equation 7), the kinetic energy of band m (i.e., the energy corresponding to the first term in equation 7 but only for the mth band), and the electron-ion energy of band m (i.e., the energy corresponding to the second term in equation 7 but only for the mth band).

The last two energies can be grouped into a matrix $H_1$ which is independent of $\rho(r)$, (referred to hereinafter as the "density-independent Hamiltonian matrix"), so that the part of the total energy which depends upon $\theta$ can be written:

$$E(\theta) = f_m\left[\left(\vec{C}_m^{i*}\cos\theta + \vec{D}^{i*}\sin\theta\right)\cdot H_1 \cdot \left(\vec{C}_m^i\cos\theta + \vec{D}^i\sin\theta\right)\right] + \quad (21)$$
$$1/2\int\int\frac{\rho(r)\rho(r')}{|r-r'|}d^3r\,d^3r' + \int\rho(r)\epsilon_{xc}(r)d^3r$$

where $f_m$ is the occupancy of band m, usually 2, and would include a k-point weight if there were more than one k-point, and where the second term is the Hartree energy and the third term is the exchange-correlation energy.

If $\rho(r)$ is expressed in terms of $\theta$ and if equation 21 is differentiated and evaluated at $\theta=0$, one obtains:

$$\left(\frac{\partial E(\theta)}{\partial \theta}\bigg|\right)_{\theta=0} = f_m\left(\vec{C}_m^{i*}\cdot H\cdot \vec{D}^i + \vec{D}^{i*}\cdot H\cdot \vec{C}_m^i\right) \quad (22)$$
$$= f_m\,2\,\text{Re}\left(\vec{D}^{i*}\cdot H\cdot \vec{C}_m^i\right)$$

From these two equations, values for the left hand sides of equation 11 can be readily obtained. Specifically, with regard to equation 22, since $$H\cdot \vec{C}_m^i$$

must be generated to obtain $\vec{D}^i$ (see equation 20 above), only a simple dot product with $\vec{D}^i$ is required to generate the first derivative of the total energy with respect to $\theta$ at $\theta=0$.

Similarly, equation 21 can be directly evaluated both at $\theta=0$ and at $\theta=\pi/300$. In this regard, it is important to note that $H_1$ is a linear operator. Thus, if one begins the ith iteration with the vector $$H_1 \cdot \vec{C}_m^i$$

and if one forms the vector $H_1\cdot\vec{D}^i$ during the ith iteration, then the expression $$H_1 \cdot \left(\vec{C}_m^i\cos\theta + \vec{D}^i\sin\theta\right)$$

in equation 21 can be readily evaluated for any $\theta$ by simply linearly combining the two vectors. Moreover, once $\theta_{min}$ has been determined, $$H_1 \cdot \vec{C}_m^{i+1}$$

can be evaluated for use in the next iteration by again linearly combining $$H_1 \cdot \vec{C}_m^i$$

and $H_1\cdot\vec{D}^i$. Thus, the density-independent Hamiltonian matrix need be applied once at the beginning of the iteration of each band and once more during each iterative cycle. This is a significant savings since the electron-ion interaction (the second term in equation 7) can be computationally intensive if non-local pseudopotentials are used.

The remainder of equation 21, i.e., the Hartree and exchange-correlation energies, must be calculated twice, i.e., for $$\vec{C}_m = \vec{C}_m^i$$

and $$\vec{C}_m = \vec{C}_m^i\cos(\pi/300) + \vec{D}^i\sin(\pi/300)$$

However, only one band density (i.e., $\rho(r)$ for the mth band) must be updated, thus making the calculation of the Hartree and exchange-correlation energies relatively easy.

It should be noted that values of $\theta$ other than $\pi/300$ can be used in performing the energy parameterization technique. In general, the value used should not be so small as to yield significant rounding error, but close enough to zero so that the curvature estimate is accurate. The value $\pi/300$ has been found to be a good compromise. Similarly, other approaches can be used to evaluate the coefficients of equation 10. For example, instead of evaluating the energy at $\pi/300$, the second derivative of the energy with respect to $\theta$ at $\theta=0$ could be used. However, a count of the operations required to do this calculation reveals that evaluating $E(\theta)$ self-consistently at some small value of $\theta$, e.g., $\pi/300$, is a slightly more efficient approach. The calculation of the second derivative, however, is somewhat less subject to rounding errors. Accordingly, overall the two approaches are considered to be similar.

III. The Reordering of the Bands

In general, the gradient/preconditioning/-conjugate-gradient/energy-parameterization sequence is repeated between 3 and 10 times, preferably 4–5 times, for the mth band. Thereafter, the remaining bands are updated following the same procedures.

After all of the bands have been updated, it is preferred to reorder the bands by forming a subspace Hamiltonian matrix using the orthogonal filled bands as basis functions. The elements of this matrix are given by:

$$\lambda_{ij} = \vec{C}_i \cdot H \cdot \vec{C}_j$$

The eigenvectors of this small matrix, e.g., 32×32 for a twelve atom silica supercell, will give the linear combinations of the trial vectors, i.e., the $\vec{C}_m$'s, which are eigenvectors in their subspace. This similarity transformation changes neither the energy nor the density of the system. However, by using the linear combination of the $\vec{C}_m$'s as the starting bands for the next set of band iterations, any problems associated with band ordering are eliminated and one is guaranteed that any subsequent change to one band which lowers its energy will be orthogonal to all of the other bands.

It should be noted that when preconditioning is performed and a Gram-Schmidt orthogonalization is used instead of the orthogonalization procedures discussed above, reordering becomes a necessary step in the process. A discussion of Gram-Schmidt orthogonalization can be found in, for example, Golub, Gene H. and Vanloan, Charles F., 1983, *Matrix Computations* (Baltimore: John Hopkins University Press).

IV. Convergence

The above process is repeated until a set of self-consistent $C_{Gn}$'s is found. A suitable numerical criterion is to require that the square of the magnitude of the $\vec{R}$ vectors of equation 20 be less than or equal to, for example, $10^{-20}$ for all of the bands. Alternatively, other criteria can be used to terminate the process. For example, convergence of the total energy of the system provides a suitable criterion. In this case, a suitable numerical criterion is to require that the change in E divided by E between two complete iterations of all the bands be less than, for example, $10^{-14}$.

As demonstrated by the examples presented below, for many problems, convergence of the energy is achieved with 20 or fewer iterations. The number of iterations required for any particular problem will of course depend upon the specifics of the material whose wavefunction is to be determined. Also, the number of iterations will depend on the level of accuracy with which the wavefunction is to be determined and/or the level of accuracy with which a physical or chemical property is to be predicted from the wavefunction. The examples illustrate this variability in the required number of iterations. Significantly, as shown by these examples, the number of iterations required by the method and apparatus of the present invention has been found to be consistently and significantly less than the number required by the fastest prior art approach developed to date.

Figure 1B:
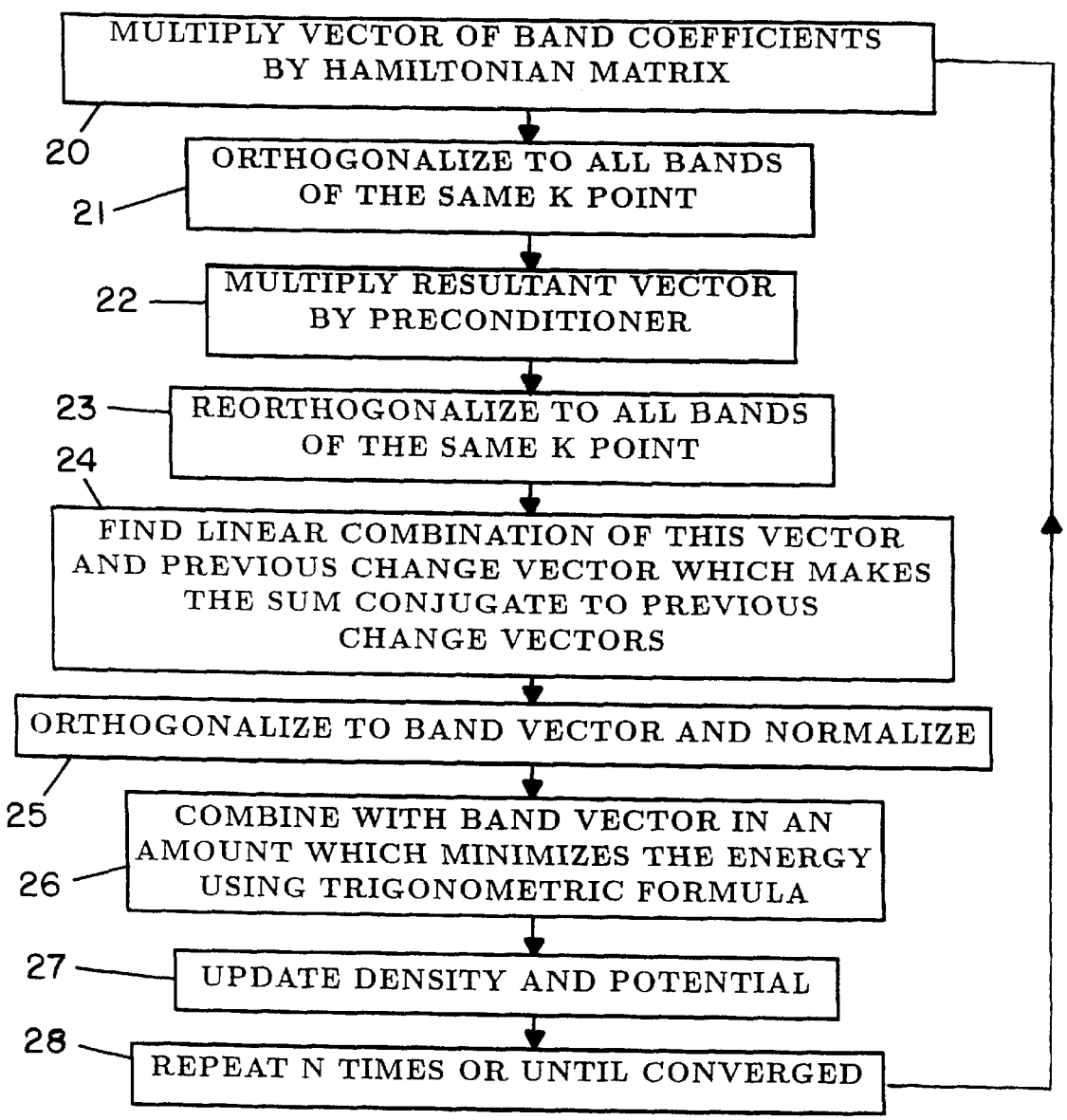

As indicated above, the invention can be implemented by the programming of a suitable digital computer, e.g, a supercomputer or a work station. FIGS. 1A and 1B set forth a preferred flow chart for such a program. Specifically, FIG. 1A shows the overall structure of the program, while FIG. 1B describes in more detail the structure of that portion of the program which updates (corrects) the $C_{Gn}$'s for a particular band and k-point, i.e., module 13 in FIG. 1A.

Module 10 in FIG. 1A comprises the initialization portion of the program. This portion inputs data regarding the atomic composition, atomic positions, and excitation state of the material whose electronic structure is to be determined, as well as data regarding the environment in which the material resides. Module 10 also selects starting values for the $C_{Gn}$'s (see Section I of the Description of the Preferred Embodiments).

The iterative portion of the program comprises modules 11 through 18. As shown in FIG. 1A, three nested iterations are performed, the outermost iteration involving changes in the locations of the atoms (modules 16 through 18) and the inner iterations involving the determination of $C_{Gn}$ values for individual bands for particular k-points (modules 11 through 15).

Upon completion of the three levels of iteration, the results of the electronic structure determination are outputted by module 19. As discussed above, the outputting can take various forms including three-dimensional displays of the material's electronic structure such as that shown in FIG. 6 for the benzene molecule (see Example 3 below).

FIG. 1B sets forth the various steps involved in the updating of the $C_{Gn}$'s for a particular band and k-point. The relationship between the modules of this flow chart and the various steps of the process discussed above is as follows: module 20 corresponds to the determination of the gradient of the energy with respect to the wavefunction parameters for the band being updated as described in section II(A); module 21 is an orthogonalization step of the type set forth in equation 20 but extended to include all bands of the k-point being updated; modules 22 and 23 comprise the preconditioning and reorthogonalization of the gradient described in section II(B); modules 24 and 25 comprise the application of the conjugate gradient technique and the subsequent orthogonalization and normalization of the resulting change vector described in section II(C); module 26 comprises the application of the energy parameterization technique described in section II(D); module 27 comprises the updating of the elements of the Hamiltonian matrix of equations 17–19 for use in performing the next iteration; and module 28 comprises the procedure for terminating the iteration of a particular band for a particular k-point, after which the program returns to module 15 of FIG. 1A.

If the optional band reordering procedure described in section III is used, an additional module is included between modules 14 and 15 to perform the reordering.

Using standard programming techniques, the flow charts of FIGS. 1A and 1B have been implemented in the FORTRAN programming language and have been successfully run on a number of commercially-available computers including a Cray XMP, a Digital VAX, an IBM 3090, a Convex C210, a Floating Point Systems Model 264, an IBM 6000 series RISC work station, and a Stellar GS 1000 work station.

Without intending to limit it in any manner, the present invention will be further described by the following examples.

EXAMPLE 1

The Accuracy of the Energy Parameterization

Figure 2:
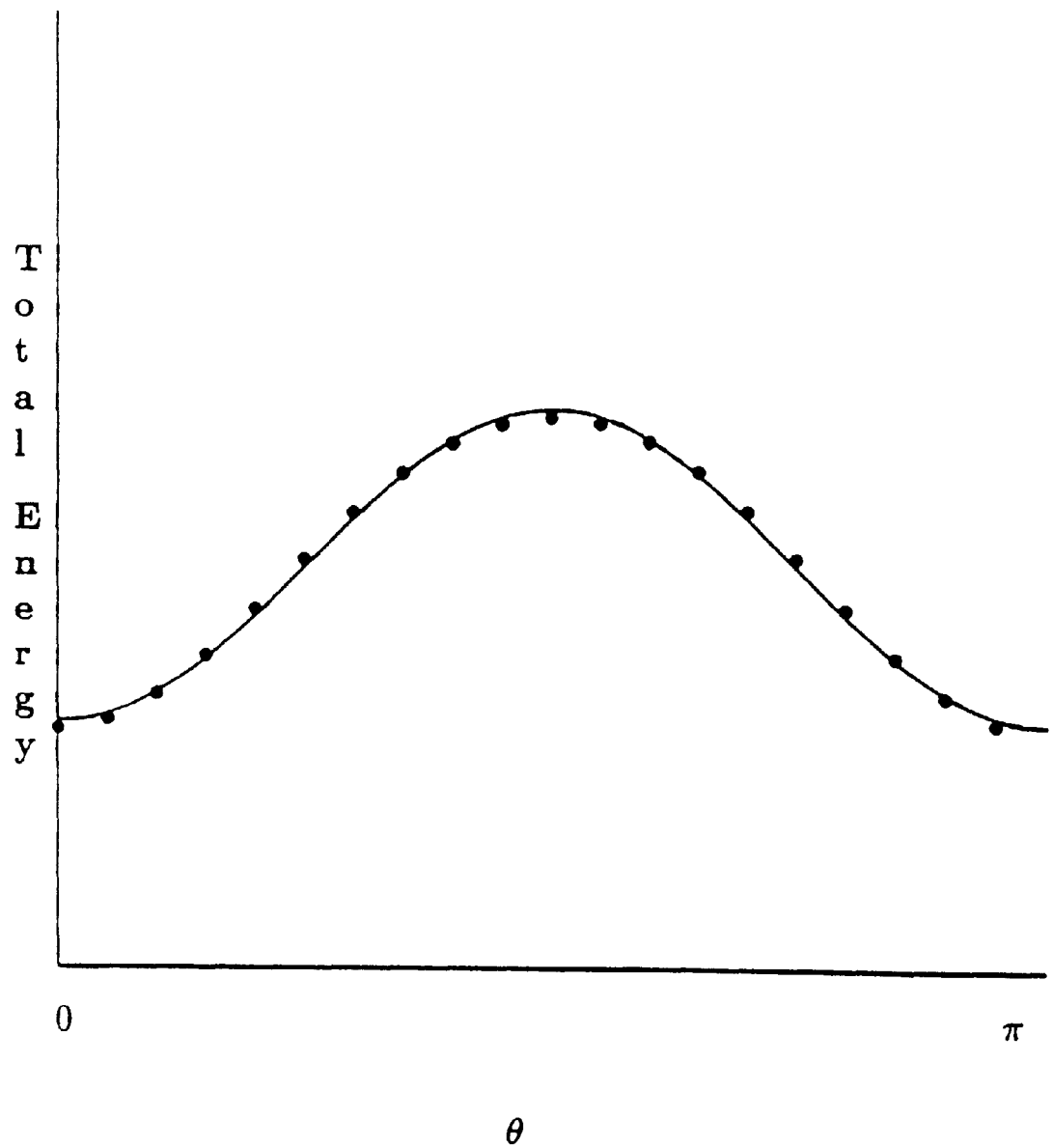
FIG. 2 is a plot of the total energy of an 8-atom silicon cube as a function of the energy parameterization variable $\theta$. The dots represent the exact calculation performed with equation 21, while the solid line represents the parameterization of equations 10 and 11.

In order to demonstrate the accuracy of the energy parameterization of equations 10 and 11, values for the total energy of an eight atom silicon cell as a function of θ when one trial vector was added were computed using equation 21. The results of these computations are shown as the dots in FIG. 2.

For the same conditions, values for $E_{avg}$, $E_{c1}$, and $E_{s1}$ were determined using the procedures described above. Using these values, the solid line of FIG. 2 was plotted. As is evident, the solid line is an excellent approximation of the functional form of E over the entire range of θ.

EXAMPLE 2

Comparative Examples

In order to demonstrate the superiority of the present invention in comparison with prior techniques, as well as to demonstrate the cumulative effects of combining together the various aspects of the invention, (i.e., energy parameterization, conjugate gradient, and preconditioning), determinations were made of the wavefunction for silicon for both a high number of plane waves and for a high number of atoms. Four methods for determining the wavefunctions were used.

The "original method" was a time integration of Schrodinger's equation in imaginary time using the semi-analytic approach of Payne et al., supra, applied to the first order scheme of Williams and Soler, supra. The approach represents the fastest approach available in the art prior to the present invention.

The other three methods used the energy parameterization aspects of the invention with three different ways of determining the vector of changes ($\vec{D}^i$) to be added to the trial vector ($\vec{C}^i$). The "steepest descents" method used the gradient vector orthogonalized to all the bands. The "conjugate gradient" method used the orthogonalized gradient vector made conjugate to earlier change vectors, i.e., it used the energy parameterization and the conjugate gradient aspects of the invention. Finally, the "preconditioned conjugate gradient" method used all three aspects of the invention, i.e., energy parameterization, conjugate gradient, and preconditioning.

As discussed above, to test the robustness of the invention, initial trial vectors were filled with random numbers and then orthonormalized. This extreme starting point ensured that every eigenvector of the Hamiltonian matrix contributed to the error.

In addition to the silicon determinations, determinations were also made for silica. In this case, only the original and preconditioned conjugate gradient methods were used.

Results

1. Determination of the Wavefunction for Silicon for a High Number of Plane Waves The first determination for silicon was performed using an 8-atom cube and planewaves up to 16 Hartrees in kinetic energy, i.e., on the order of 2000 plane waves. The normal maximum kinetic energy used for silicon lies in the 4–6 Hartree region, i.e., on the order of 250 plane waves. Many other materials, however, require much higher kinetic energy plane waves (e.g., silica requires plane waves of approximately 20 Hartrees). This example was thus designed to test the ability of the present invention to handle such higher energy plane waves.

Figure 3:
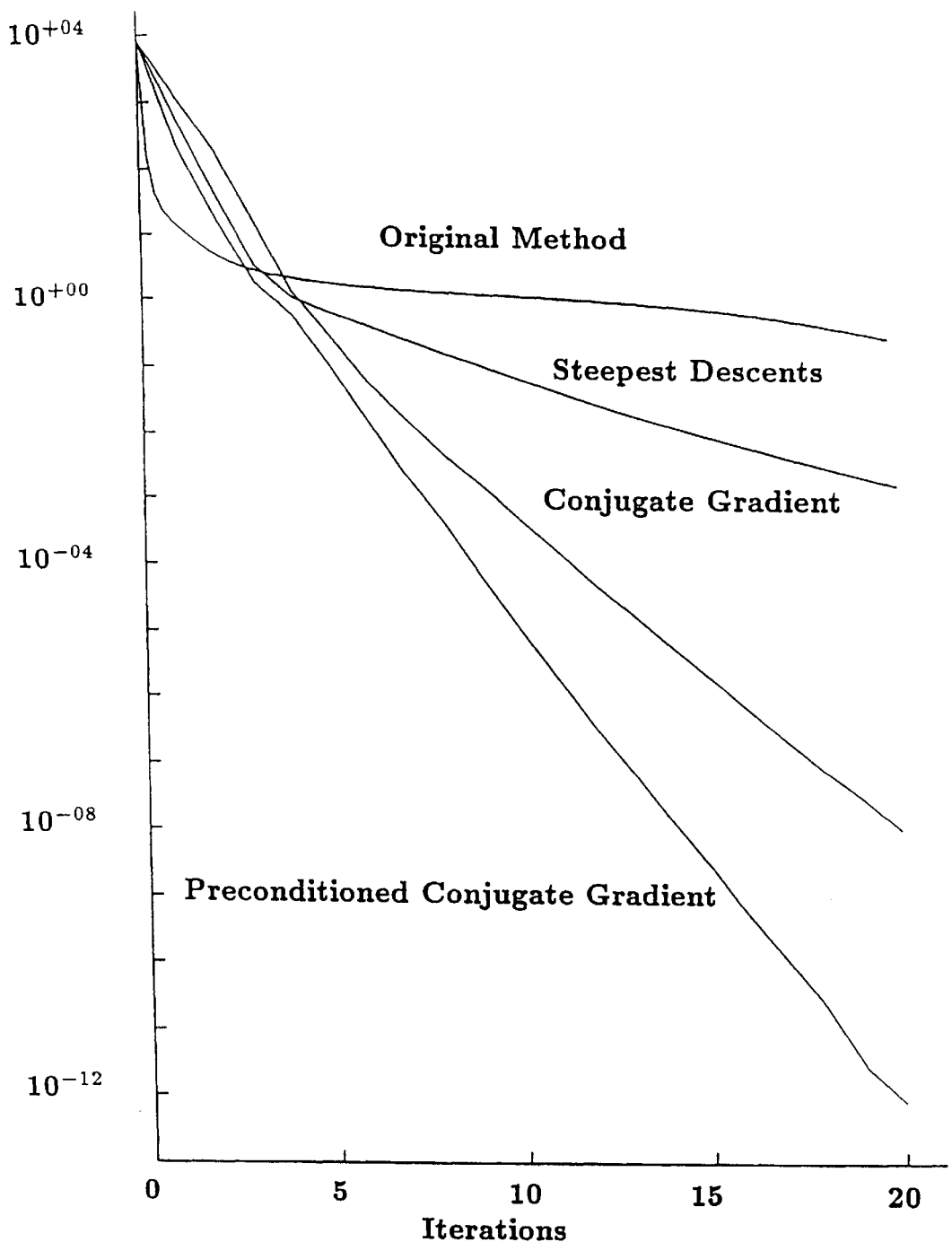
FIG. 3 is a plot of total energy error in eV versus iteration number determined from the wavefunction for an 8-atom silicon cube using plane waves of up to 16 Hartrees of kinetic energy and using 1) a prior technique identified as the "Original Method" and 2) three techniques embodying various aspects of the present invention and identified as "Steepest Descents", "Conjugate Gradient", and "Preconditioned Conjugate Gradient".

FIG. 3 shows the results of applying all four methods. The number of iterations plotted is 100 for the original method and 20 for each of the steepest descents, conjugate gradient, and preconditioned conjugate gradient methods. The original method applied the gradient operator once per time step. The methods using energy parameterization typically updated each band four times per iteration which took additional time. The difference in scales for the original method and the energy parameterization methods make the computation time roughly equal for all the methods.

As shown in FIG. 3, each of the methods using energy parameterization was significantly better than the original method. All three of the energy parameterization techniques were able to handle the high number of plane waves used in this example. Among the three techniques, the preconditioned conjugate gradient technique exhibited the highest rate of convergence, followed by the conjugate gradient technique and then the steepest descents technique.

2. Determination of the Wavefunction for Silicon for a High Number of Atoms

The second determination for silicon was performed using a row of 12 silicon unit cells with 24 atoms, i.e., two atoms per cell, and a maximum kinetic energy of 4 Hartrees. The results are shown in FIG. 4 where again the scales for the original method and the methods employing energy parameterization differ by a factor of 5.

As shown in this figure, the convergence was extremely slow using the original method. To avoid charge oscillations, the time step had to be cut by a factor of 150 over that used in a 2-atom unit cell. Thousands of iterations were necessary for convergence.

Figure 4:
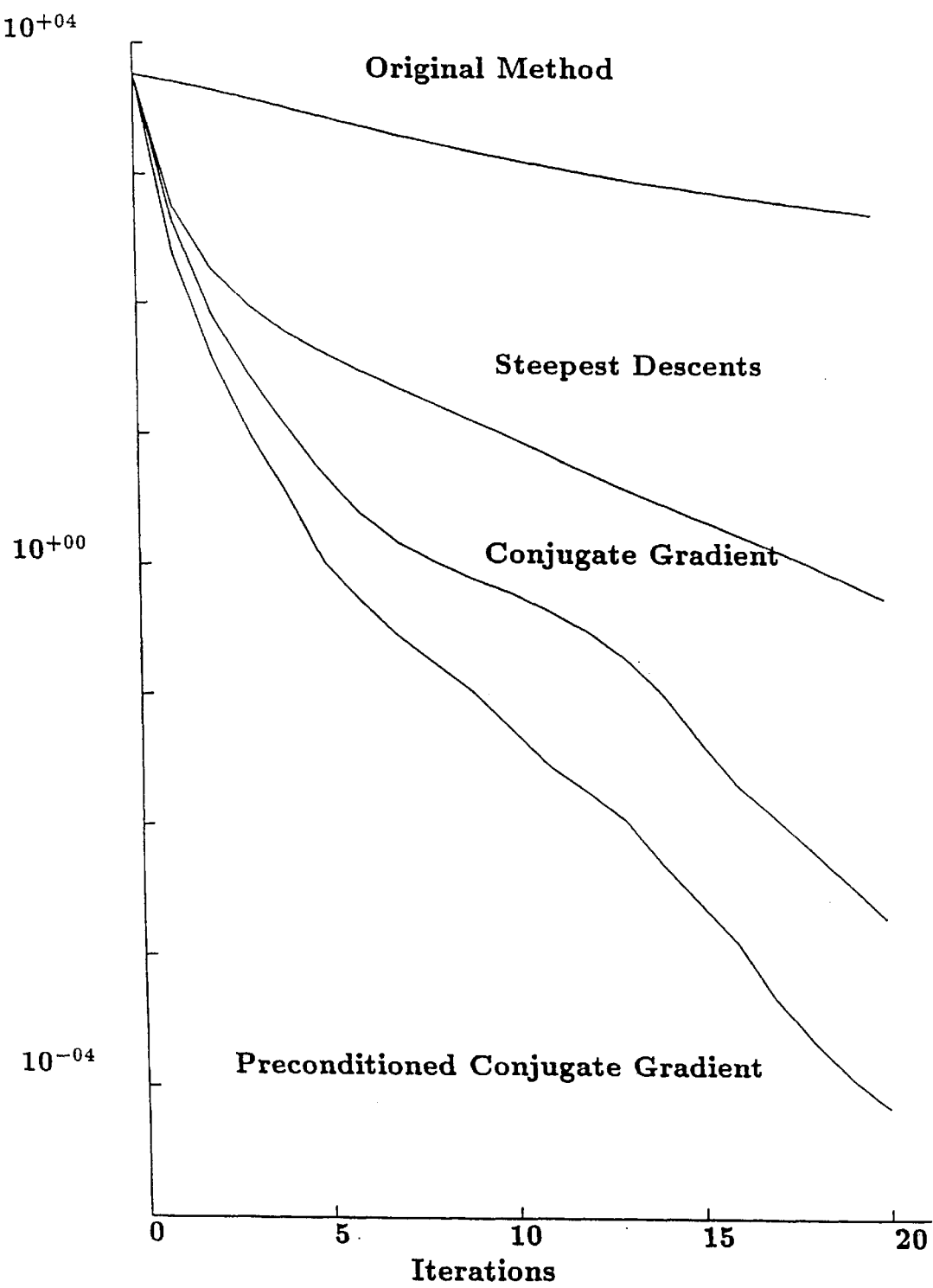
FIG. 4 is a plot of total energy error in eV versus iteration number determined from the wavefunction for a row of 12 silicon unit cells, each cell including two atoms, using plane waves of up to 4 Hartrees of kinetic energy and using the four techniques of FIG. 3.

As may be seen in FIG. 4, each of the energy parameterization techniques constitutes an enormous improvement over the original technique. Also, as with the high number of plane waves, the preconditioned conjugate gradient method is again significantly more efficient than the others.

3. Determination of the Wavefunction for Silica

Figure 5:
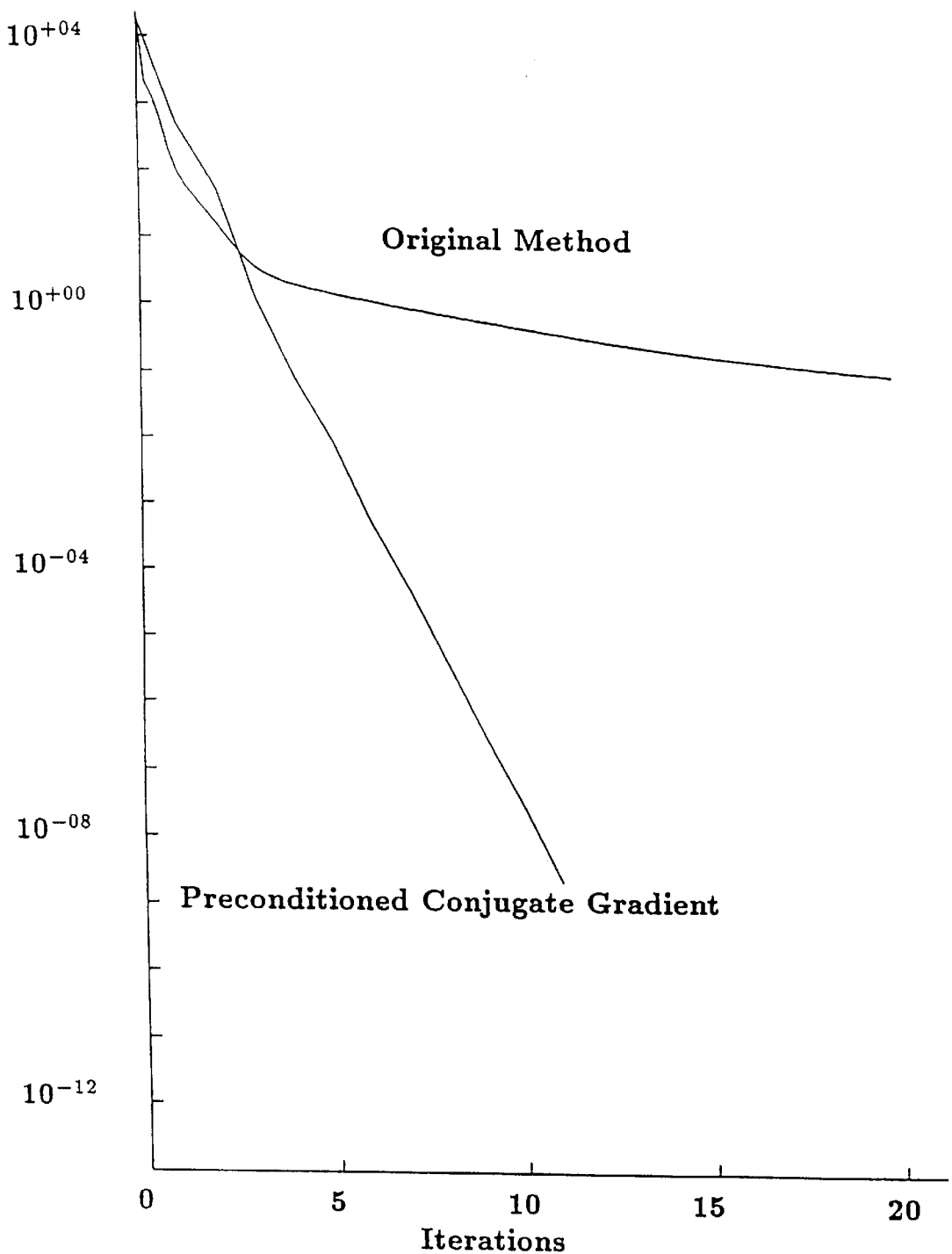
FIG. 5 is a plot of total energy error in eV versus iteration number determined from the wavefunction for a 12 atom cell of the alpha-cristobalite form of $SiO_2$ using plane waves of up to 16 Hartrees of kinetic energy and using 1) the "Original Method" and 2) the "Preconditioned Conjugate Gradient" technique.

The wavefunction for the alpha-cristobalite form of $SiO_2$ was determined using a twelve atom unit cell and plane waves of up to 16 Hartrees of energy. The original and preconditioned conjugate gradient techniques were tested. The results are shown in FIG. 5, where again 20 iterations for the preconditioned conjugate gradient method are plotted versus 100 iterations for the original method to roughly normalize the computational effort.

As shown in this figure, the preconditioned conjugate gradient method is again significantly better than the original method. Indeed, after only 11 iterations, the determination of the total energy using the preconditioned conjugate gradient method had reached the limit of rounding error. Thereafter, the errors in the wavefunction continued to be lowered even though the total energy could not be determined more accurately.

This convergence of the energy determination in 11 iterations constitutes a clear and dramatic demonstration of the power of the present invention since the determination of the wavefunction for silica is considered a challenging problem in the art.

EXAMPLE 3

Determination of the Electronic Structure of Benzene

This example illustrates the use of the present invention to determine the electronic structure of complex materials. The benzene molecule ($C_6H_6$) was chosen to illustrate the process. The structure of this molecule was determined using 15 doubly-occupied bands and 5,000 plane waves per band. The total number of $C_{Gn}$'s was thus 75,000. The calculations were performed with the carbon nuclei at their experimentally reported positions.

Approximately 10 iterations were performed through the bands with each band being individually iterated 4 times for each pass. The total computing time required for these calculations was on the order of 10–12 hours on a Stellar GS 1000 work station.

Figure 6:
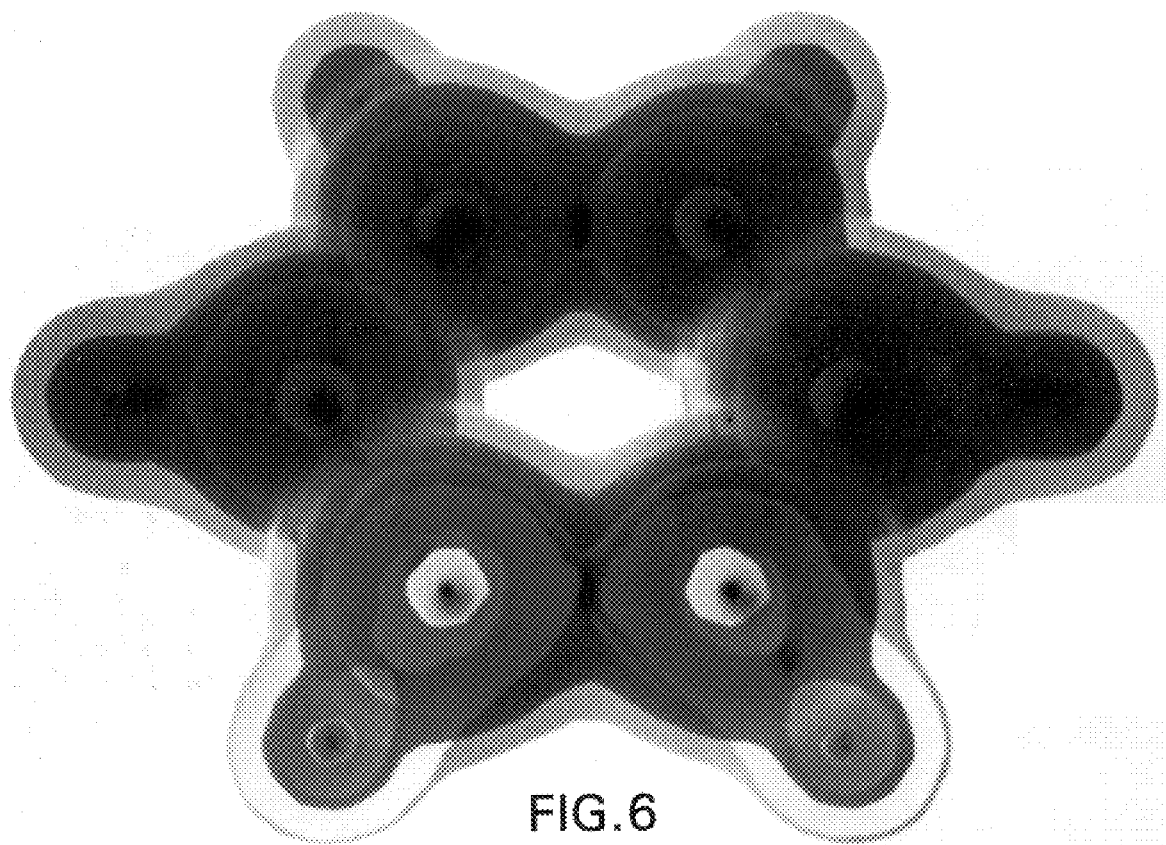
FIG. 6 illustrates the three-dimensional configuration of the electronic structure of the benzene molecule as determined in accordance with the present invention.

The final set of $C_{Gn}$ values obtained by this process was used with equation 5 to construct a display of the three-dimensional configuration of the benzene electronic structure. The original display employed four colors with each color representing a different electron probability density level. FIG. 6 is a black and white photograph of the original color display. The transformation from color to black and white has caused some asymmetries to appear in the photograph. In the original color display, all of the carbon-hydrogen pairs are identical.

FIG. 6 clearly shows the increased electron probability densities in the regions of the six carbon nuclei lying at the center of the molecule. Similarly, the increased electron probability densities in the regions of the six surrounding hydrogen nuclei are also shown. In the original color display, the electron probability densities in the regions of the carbon nuclei are substantially above those in the regions of the hydrogen nuclei, as would be expected. The reactive lobes extending from the hydrogen nuclei are also clearly evident in this photograph.

This example illustrates the ability of the present invention to provide precise physical and chemical data in an economical manner. The electronic structure for benzene shown in FIG. 6 represents one of numerous applications of the invention. Following the procedures used for benzene, electronic structures and physical and chemical properties of other complex materials can be readily determined.

Although specific embodiments of the invention have been described and illustrated, it is to be understood that modifications can be made without departing from the invention's spirit and scope. For example, other energy parameterizations which are substantially accurate to second order can be used in place of the parameterization of equation 10. In particular, polynomial expansions can be used for this purpose. Similarly, other energy operators besides that set forth in equation 7 and thus other Hamiltonian matrices besides that of equation 17 can be used in the practice of the invention. In particular, the invention is applicable to other formulations of the exchange-correlation energy besides the local density approximation. For example, the GW theory of Hedin and Lundquist, *Solid State Physics*, Vol. 23, page 1, 1969, can significantly improve the error in the local density approximation although at the cost of an order of magnitude increase in computation time. Similarly, other wavefunction expansions besides the one set forth in equation 8 can be used. In particular, a Gaussian expansion of the wavefunction can be used with the energy parameterization and conjugate gradient aspects of the invention. Other modifications of these and other types will be evident to persons of ordinary skill in the art from the disclosure herein.

What is claimed is:

1. A method for displaying the structure of a material comprising the steps of:
   (A) inputting data into a computer system regarding the atomic composition, atomic positions, and excitation state of the material and the environment in which the material resides;
   (B) selecting an expression for the wavefunction describing the electrons of the material, said expression being a product of component wavefunctions, each of the component wavefunctions including a linear combination of plane waves, each plane wave being characterized by a spatial frequency and direction and being multiplied by a wavefunction parameter;
   (C) iteratively determining values for the wavefunction parameters by means of a programmed computer by:
      (I) changing the wavefunction parameters for one of the component wavefunctions while holding the wavefunction parameters of the remaining component wavefunctions constant by iteratively performing the steps of:
         (a) calculating values for the components of the gradient of the energy of the electrons of the material with respect to the wavefunction parameters of the wavefunction component being changed;
         (b) conditioning the values calculated in step (C) (I) (a) by reducing some of those values relative to others of those values, the values which are reduced corresponding to plane waves having higher spatial frequencies than the spatial frequencies corresponding to the values which are not reduced;
         (c) determining from the conditioned values obtained in step (C) (I) (b), a set of changes to the wavefunction parameters of the wavefunction component being changed; and
         (d) forming a changed set of wavefunction parameters for the wavefunction component being changed from the set of changes determined in step (C) (I) (c);
      (II) performing step (C) (I) for each of the other component wavefunctions; and
      (III) repeating steps C (I) and C (II) until the wavefunction parameters satisfy a predetermined criterion;
   (D) determining a structure for the material using the wavefunction expression selected in step (B) and the wavefunction parameters determined in step (C); and
   (E) displaying the structure determined in step (D).

2. The method of claim 1 wherein step (C) (I) (b) includes the step of multiplying the values determined in step (C) (I) (a) by a function which grows as one over the square of the spatial frequency as the spatial frequency becomes large.

3. The method of claim 1 wherein step (C) (I) (b) includes the steps of:
   (i) determining a kinetic energy value for each plane wave, said kinetic energy value being a function of the spatial frequency of the plane wave;
   (ii) determining a kinetic energy expectation value for the linear combination of the plane waves of the wavefunction component being changed; and
   (iii) multiplying each value determined in step (C) (I) (a) by a function of the ratio (x) of (a) the kinetic energy value determined in step (i) for the plane wave corresponding to that value to (b) the kinetic energy expectation value determined in step (ii).

4. The method of claim 1 wherein step (C) (I) (c) is performed using the conjugate gradient technique.

5. The method of claim 1 including the additional step between steps (C) (II) and (C) (III) of reordering the wavefunction components.

6. The method of claim 1 wherein the expression for the wavefunction includes k-points and wherein in step (C), values for the wavefunction parameters are obtained for each of the k-points.

7. The method of claim 1 including the additional step after step (C) of adjusting the atomic positions based on the values of the wavefunction parameters determined in step (C) and repeating step (C) until the atomic positions and the values of the wavefunction parameters are self-consistent.

8. A method for displaying the structure of a material comprising the steps of:
   (A) inputting data into a computer system regarding the atomic composition, atomic positions, and excitation state of the material and the environment in which the material resides;
   (B) selecting an expression for the wavefunction describing the electrons of the material, said expression including a linear combination of plane waves, each plane wave being characterized by a spatial frequency and direction and being multiplied by a wavefunction parameter;
   (C) iteratively determining values for the wavefunction parameters by means of a programmed computer by:
      (I) selecting a first set of trial values for the wavefunction parameters;
      (II) forming expressions for the components of the gradient of the energy of the electrons of the material with respect to the wavefunction parameters and evaluating the expressions for the wavefunction parameters equal to the first set of trial values, said expressions depending upon the inputted data, the wavefunction parameters, and the spatial frequencies of the plane waves;
      (III) conditioning the components of the gradient by reducing the values of some of those components relative to the values of others of those components, the values which are reduced corresponding to plane waves having higher spatial frequencies than the spatial frequencies corresponding to the values which are not reduced;
      (IV) determining from the conditioned components of the gradient obtained in step (C) (III), a set of changes to the first set of trial values;
      (V) determining a second set of trial values for the wavefunction parameters by combining the first set of trial values with the set of changes; and (VI) repeating steps (C) (I) through (C) (V) using the second set of trial values determined in step (C) (V) as the first set of trial values in step (C) (I) until the wavefunction parameters satisfy a predetermined criterion;

(D) determining a structure for the material using the wavefunction expression selected in step (B) and the wavefunction parameters determined in step (C); and (E) displaying the structure determined in step (D).

9. A method for displaying the structure of a material comprising the steps of:

(A) inputting data into a computer system regarding the atomic composition, atomic positions, and excitation state of the material and the environment in which the material resides;

(B) selecting an expression for the wavefunction describing the electrons of the material, said expression being a product of component wavefunctions and including a set of wavefunction parameters;

(C) iteratively determining values for the set of wavefunction parameters by means of a programmed computer by:

(I) changing the wavefunction parameters for one of the component wavefunctions while holding the wavefunction parameters for the remaining component wavefunctions constant by iteratively performing the steps of:

(a) calculating values for the components of the gradient of the energy of the electrons of the material with respect to the wavefunction parameters of the wavefunction component being changed;

(b) determining from the values obtained in step (C) (I) (a), a set of changes to the wavefunction parameters of the wavefunction component being changed; and (c) forming a changed set of wavefunction parameters for the wavefunction component being changed from the set of changes determined in step (C) (I) (b), said changed set of wavefunction parameters minimizing a parameterized expression for the energy of the electrons of the material which is substantially accurate to second order;

(II) performing step (C) (I) for each of the other component wavefunctions; and (III) repeating steps C(I) and C(II) until the wavefunction parameters satisfy a predetermined criterion;

(D) determining a structure for the material using the wavefunction expression selected in step (B) and the set of wavefunction parameters determined in step (C); and (E) displaying the structure determined in step (D).

10. The method of claim 9 wherein the parameterized expression (E) for the energy of the electrons of the material is of the form:

$$E(\theta) = E_{avg} + E_{c1} \cos 2\theta + E_{s1} \sin 2\theta$$

where E, $E_{avg}$, $E_{c1}$, and $E_{s1}$ are energy parameters and $\theta$ is an energy parameterization variable.

11. The method of claim 10 wherein values for the energy parameters are determined by:

(i) obtaining a value for the portion of the energy of the electrons of the material which depends on the set of changes for the energy parameterization variable equal to zero;

(ii) obtaining a value for the portion of the energy of the electrons of the material which depends on the set of changes for the energy parameterization variable having a value greater than zero; and (iii) obtaining a value for the first derivative of the portion of the energy of the electrons of the material which depends on the set of changes with respect to the energy parameterization variable, said value being obtained for the energy parameterization variable equal to zero.

12. The method of claim 9 wherein step (C) (I) (b) is performed using the conjugate gradient technique.

13. The method of claim 9 including the additional step between steps (C) (II) and (C) (III) of reordering the wavefunction components.

14. The method of claim 9 wherein the expression for the wavefunction includes k-points and wherein in step (C), values for the wavefunction parameters are obtained for each of the k-points.

15. The method of claim 9 including the additional step after step (C) of adjusting the atomic positions based on the values of the set of wavefunction parameters determined in step (C) and repeating step (C) until the atomic positions and the values of the set of wavefunction parameters are self-consistent.

16. A method for displaying the structure of a material comprising the steps of:

(A) inputting data into a computer system regarding the atomic composition, atomic positions, and excitation state of the material and the environment in which the material resides;

(B) selecting an expression for the wavefunction describing the electrons of the material, said expression including a set of wavefunction parameters;

(C) iteratively determining values for the set of wavefunction parameters by means of a programmed computer by:

(I) selecting a first set of trial values for the wavefunction parameters;

(II) forming expressions for the components of the gradient of the energy of the electrons of the material with respect to the wavefunction parameters and evaluating the expressions for the wavefunction parameters equal to the first set of trial values, said expressions depending upon the inputted data and the set of wavefunction parameters;

(III) determining from the components of the gradient evaluated in step (C) (II), a set of changes to the first set of trial values;

(IV) determining a second set of trial values for the wavefunction parameters by combining a portion of the first set of trial values with a portion of the set of changes, said portions being described by a variable, the value of the variable being determined by:

(a) selecting an expression for the energy of the electrons of the material in terms of the variable, said expression being substantially accurate to second order and including a set of energy parameters;

(b) determining values for the energy parameters using the first set of trial values, the set of changes, and the inputted data; and (c) using the values of the energy parameters determined in step (C) (IV) (b) to determine the value of the variable which minimizes the energy expression; and (V) repeating steps (C) (I) through (C) (IV) using the second set of trial values determined in step (C) (IV)

as the first set of trial values in step (C) (I) until the wavefunction parameters satisfy a predetermined criterion;

(D) determining a structure for the material using the wavefunction expression selected in step (B) and the set of wavefunction parameters determined in step (C); and (E) displaying the structure determined in step (D).

17. A method for displaying the structure of a material comprising the steps of:

(A) inputting data into a computer system regarding the atomic composition, atomic positions, and excitation state of the material and the environment in which the material resides;

(B) expressing the wavefunction of the material in terms of wavefunction parameters;

(C) determining values for the wavefunction parameters using a programmed computer, the data of step (A), and the conditioning the gradient technique;

(D) determining a structure for the material using the wavefunction expression selected in step (B) and the wavefunction parameters determined in step (C); and (E) displaying the structure determined in step (D).

18. A method for displaying the structure of a material comprising the steps of:

(A) inputting data into a computer system regarding the atomic composition, atomic positions, and excitation state of the material and the environment in which the material resides;

(B) expressing the wavefunction of the material in terms of wavefunction parameters;

(C) determining values for the wavefunction parameters using a programmed computer, the data of step (A), and a parameterized expression for the energy of the electrons of the material which is substantially accurate to second order;

(D) determining a structure for the material using the wavefunction expression selected in step (B) and the wavefunction parameters determined in step (C); and (E) displaying the structure determined in step (D).

19. The method of claim 18 wherein step (C) employs the conditioning the gradient technique.

20. The method of claim 19 wherein step (C) employs the conjugate gradient technique.

* * * * *

UNITED STATES PATENT AND TRADEMARK OFFICE
CERTIFICATE OF CORRECTION

PATENT NO. : 6,106,562  
DATED : August 26, 1992  
INVENTOR(S) : Michael P. Teter and Michael C. Payne Page 1 of 1

It is certified that error appears in the above-identified patent and that said Letters Patent is hereby corrected as shown below:

<u>Column 6,</u>  
Line 36, $\vec{G} \cdot \vec{1} = n_i$ should read $\vec{G} \cdot \vec{1}_i = n_i$ Signed and Sealed this Sixteenth Day of April, 2002

Attest:

JAMES E. ROGAN  
*Attesting Officer*  *Director of the United States Patent and Trademark Office*